United States Patent
Ji et al.

(10) Patent No.: US 10,633,705 B2
(45) Date of Patent: Apr. 28, 2020

(54) N-ACETYL-ALPHA-D-GLUCOSAMINIDASE DEFICIENCY COMPOSITIONS AND METHODS

(71) Applicant: ALEXION PHARMACEUTICALS, INC., New Haven, CT (US)

(72) Inventors: Rui-Ru Ji, Belmont, MA (US); Andrew Hutchinson, Stamford, CT (US); Nina Jain, North Andover, MA (US); Christen D. Forbes, North Haven, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 15/730,382

(22) Filed: Oct. 11, 2017

(65) Prior Publication Data
US 2018/0105879 A1    Apr. 19, 2018

Related U.S. Application Data

(60) Provisional application No. 62/455,905, filed on Feb. 7, 2017, provisional application No. 62/408,281, filed on Oct. 14, 2016.

(51) Int. Cl.
| | |
|---|---|
| *C12Q 1/68* | (2018.01) |
| *C12Q 1/6883* | (2018.01) |
| *A61K 38/47* | (2006.01) |

(52) U.S. Cl.
CPC ............ *C12Q 1/6883* (2013.01); *A61K 38/47* (2013.01); *C12Y 302/0105* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,663,631 B2 | 3/2014 | Quinn | |
| 8,775,146 B2 | 7/2014 | Meiyappan et al. | |
| 2012/0021436 A1* | 1/2012 | Meiyappan ............... | C12Q 1/34 435/7.8 |
| 2013/0095092 A1* | 4/2013 | Quinn ..................... | A61K 38/47 424/94.61 |
| 2013/0209436 A1 | 8/2013 | Quinn et al. | |
| 2014/0155475 A1 | 6/2014 | Bancel et al. | |
| 2017/0216413 A1 | 8/2017 | Quinn et al. | |

FOREIGN PATENT DOCUMENTS

| | | |
|---|---|---|
| WO | WO 2011/133960 A2 | 10/2011 |
| WO | WO 2012/050695 A1 | 4/2012 |
| WO | WO 2013/055888 A2 | 4/2013 |
| WO | WO 2016/054025 A1 | 4/2016 |
| WO | WO 2017/132675 A1 | 8/2017 |

OTHER PUBLICATIONS

Tessitor et al. (Hum Genet 2000 vol. 107 p. 568) (Year: 2000).*
U.S. Appl. No. 16/073,529, filed Jul. 27, 2018, Rojas-Caro et al.
"SBC-103 (rhNAGLU Enzyme) Shows a 26.2 Percent Mean Reduction in Heparan Sulfate in Cerebrospinal Fluid at the Highest Dose Studied in Patients with Mucopolysaccharidosis IIIB (MPS IIIB) in Phase 1/2 Study at Six Months." Press Release Distribution, EDGAR Filing, XBRL, Regulatory Filings. Business Wire, Mar. 1, 2016. [retrieved on Aug. 24, 2018]. Retrieved from the Internet: <URL: businesswire.com/news/home/20160301006917/en/SBC-103-rhNAGLU-enzyme-Shows-26.2-Percent-Reduction>. 4 pages.
"Alexion Presents New SBC-103 (rhNAGLU Enzyme) Phase 1/2 Data on Brain MRI and Neurocognitive Assessments in Patients with Mucopolysaccharidosis IIIB (MPS IIIB)." Press Release Distribution, EDGAR Filing, XBRL, Regulatory Filings. Business Wire, Jul. 14, 2016. [retrieved on Aug. 24, 2018]. Retrieved from the Internet: <URL: businesswire.com/news/home/20160714005680/en/>. 5 pages.
Amberger et al., "McKusick's Online Mendelian Inheritance in Man (OMIM®)," *Nucleic Acids Res*, Jan. 2009; 37(Database issue): D793-D796.
National Center for Biotechnology Information, National Library of Medicine, National Institutes of Health, GenBank Locus NM_000263, Accession No. NM_000263, "*Homo sapiens* N-acetyl-alpha-glucosaminidase (NAGLU), mRNA," [online]. Bethesda, MD [retrieved on Oct. 5, 2018]. Retrieved from the Internet: <URL: ncbi.nlm.nih.gov/nuccore/NM_000263.3>; 4 pgs.
Chial et al., "Rare Genetic Disorders: Learning About Genetic Disease Through Gene Mapping, SNPs, and Microarray Data," *Nature Education*, 2008; 1(1):192. [retrieved on Aug. 30, 2018] from the Internet. Retrieved from the Internet:<URL:nature.com/scitable/topicpage/rare-genetic-disorders-learning-about-genetic-disease-979>; 5 pgs.
Chow et al., "4-Methylumbelliferyl 2-acetamido-2-deoxy-alpha-D-glucopyranoside, a fluorogenic substrate for N-acetyl-alpha-D-glucosaminidase," *Carbohydr Res*, Oct. 1, 1981; 96(1):87-93.
Dekaban, "Changes in brain weights during the span of human life: relation of brain weights to body heights and body weights," *Ann Neurol*, Oct. 1978; 4(4):345-56.
Heron et al., "Incidence and natural history of mucopolysaccharidosis type III in France and comparison with United Kingdom and Greece," *Am J Med Genet A*, Jan. 2011; 155A(1):58-68.
Johanson et al. "Multiplicity of cerebrospinal fluid functions: New challenges in health and disease," *Cerebrospinal Fluid Res*, May 14, 2008; 5:10.

(Continued)

*Primary Examiner* — Katherine D Salmon

(74) *Attorney, Agent, or Firm* — Mueting, Raasch & Gebhardt, P.A.

(57) ABSTRACT

Compositions and methods relating to potentially pathogenic mutations in the nucleotide sequence of a human NAGLU gene. Some NAGLU gene variants have been discovered to be associated with reduced N-acetyl-α-D-glucosaminidase (NAGLU) activity.

20 Claims, 3 Drawing Sheets

Specification includes a Sequence Listing.

(56) References Cited

OTHER PUBLICATIONS

LeBowitz et al., "Utilizing activity assays and population-wide allele frequencies to assess the contribution of novel mutations in NAGLU to MPS IIIB incidence," *Molecular Gen Metab*, Feb. 2016; 117(2):S72.

Marsh et al., "4-Methylumbelliferyl alpha-N-acetylglucosaminidase activity for diagnosis of Sanfilippo B disease," *Clin Genet*, Mar. 1985; 27(3):258-62.

Mauri et al., "A rapid and sensitive method for measuring N-acetylglucosaminidase activity in cultured cells," *PLoS One*, Jun. 28, 2013; 8(6):e60860.

Pabinger et al., "A survey of tools for variant analysis of next-generation genome sequencing data," *Brief Bioinform*, Mar. 2014; 15(2):256-78. Epub Jan. 21, 2013.

4-Methylumbelliferyl N-acetyl-α-D-glucosaminide M 9881. Product Information [online]. SIGMA-Aldrich, Inc. Jan. 2004; [retrieved on Aug. 24, 2018]. Retrieved from the Internet: <URL: sigmaaldrich.com/content/dam/sigma-aldrich/docs/Sigma/Product_Information_Sheet/l/m9881pis.pdf>. 2 pages.

Sambrook et al., *Molecular cloning: a laboratory manual*, $2^{nd}$ ed. Cold Spring Harbor Laboratory Press: Cold Spring Harbor, New York; 1989. Cover page, title page, and table of contents. 31 pages.

Sly et al., "Enzyme therapy in mannose receptor-null mucopolysaccharidosis VII mice defines roles for the mannose 6-phosphate and mannose receptors," *Proc Natl Acad Sci USA*, Oct. 10, 2006; 103(41):15172-7. Epub Oct. 2, 2006.

Universal Protein Resource (UniProt), UniProt Consortium, Accession No. P54802 ANAG_Human [retrieved on Oct. 5, 2018]. Retrieved from the Internet: <URL: uniprot.org/uniprot/P54802>. 1 page.

Weber et al., "Expression and characterization of human recombinant and alpha-N-acetylglucosaminidase," *Protein Expr Purif*, Mar. 2001; 21(1):251-9.

Whitley et al., "Initial, 24 Week Results of Heparan Sulfate Levels in Cerebrospinal Fluid (CSF) and Serum in an Open Label, Phase I/II, First-in-Human Clinical Trial of Intravenous SBC-103 in Mucopolysaccharidosis IIIB," Poster presented at World Symposium Annual Meeting 2016, San Diego, Feb. 29-Mar. 4.

Whitley et al., Abstract LB-33: "Initial, 24 Week Results of Heparan Sulfate Levels in Cerebrospinal Fluid (CSF) and Serum in an Open Label, Phase I/II, First-in-Human Clinical Trial of Intravenous SBC-103 in Mucopolysaccharidosis IIIB," World Symposium Annual Meeting 2016, San Diego, Feb. 29-Mar. 4. 1 page.

Whitley et al., "Initial, 24 Week Results of Heparan Sulfate Levels in Cerebrospinal Fluid (CSF) and Serum, Brain Structural MRI and Neurocognitive Evaluations in a Phase I/II, First-in-Human Clinical Trial of Intravenous SBC-103 in Mucopolysaccharidosis IIIB" Poster presented at 14th International Symposium on MPS and Related Diseases 2016, Bonn, Germany, Jul. 14-17. 1 page.

Whitley et al., Abstract No. 99: "Initial, 24 Week Results of Heparan Sulfate Levels in Cerebrospinal Fluid (CSF) and Serum, Brain Structural MRI and Neurocognitive Evaluations in a Phase I/II, First-in-Human Clinical Trial of Intravenous SBC-103 in Mucopolysaccharidosis IIIB" 14th International Symposium on MPS and Related Diseases 2016, Bonn, Germany, Jul. 14-17. 1 page.

Wijburg et al., "Mucopolysacchardosis type III (Sanfilippo syndrome) and misdiagnosis of idiopathic developmental delay, attention deficit/hyperactivity disorder or autism spectrum disorder," *Acta Paediatr*, May 2013;102(5):462-70.

\* cited by examiner

Human NAGLU Amino Acid Sequence

```
1   MEAVAVAAAV GVLLLAGAGG AAGDEAREAA AVRALVARLL GPGPAADFSV SVERALAAKP

61  GLDTYSLGGG GAARVRVRGS TGVAAAAGLH RYLRDFCGCH VAWSGSQLRL PRPLPAVPGE

121 LTEATPNRYR YYQNVCTQSY SFVWWDWARW EREIDWMALN GINLALAWSG QEAIWQRVYL

181 ALGLTQAEIN EFFTGPAFLA WGRMGNLHTW DGPLPPSWHI KQLYLQHRVL DQMRSFGMTP

241 VLPAFAGHVP EAVTRVFPQV NVTKMGSWGH FNCSYSCSFL LAPEDPIFPI IGSLFLRELI

301 KEFGTDHIYG ADTFNEMQPP SSEPSYLAAA TTAVYEAMTA VDTEAVWLLQ GWLFQHQPQF

361 WGPAQIRAVL GAVPRGRLLV LDLFAESQPV YTRPASFQGQ PFIWCMLHNF GGNHGLFGAL

421 EAVNGGPEAA RLFPNSTMVG TGMAPEGISQ NEVVYSLMAE LGWRKDPVPD LAAWVTSFAA

481 RRYGVSHPDA GAAWRLLLRS VYNCSGEACR GHNRSPLVRR PSLQMNTSIW YNRSDVFEAW

541 RLLLTSAPSL ATSPAFRYDL LDLTRQAVQE LVSLYYEEAR SAYLSKELAS LLRAGGVLAY

601 ELLPALDEVL ASDSRFLLGS WLEQARAAAV SEAEADFYEQ NSRYQLTLWG PEGNILDYAN

661 KQLAGLVANY YTPRWRLFLE ALVDSVAQGI PFQQHQFDKN VFQLEQAFVL SKQRYPSQPR

721 GDTVDLAKKI FLKYYPRWVA GSW
```

(SEQ ID NO:1)

*FIG. 1*

Human NAGLU cDNA Sequence

```
   1    atggaggcgg tggcggtggc cgcggcggtg gggtccttc tcctggccgg
  51    ggccggggc gcggcaggcg acgaggcccg ggaggcggcg gccgtgcggg
 101    cgctcgtggc ccggctgctg gggcaggcc cgcggccga cttctccgtg
 151    tcggtggagc gcgctctggc tgccaagccg ggcttggaca cctacagcct
 201    gggcggcggc ggcgcggcgc cgtgcgggt gcgcggctcc acgggcgtgg
 251    cggccgccgc ggggctgcac cgctacctgc gcgacttctg tggctgccac
 301    gtggcctggt ccggctctca gctgcgcctg ccgcggccac tgccagccgt
 351    gccggggag ctgaccgagg ccacgcccaa caggtaccgc tattaccaga
 401    atgtgtcac gcaaagctac tctttcgtgt ggtgggactg ggcccgctgg
 451    gagcgagaga tagactggat ggcgctgaat ggcatcaacc tggcactggc
 501    ctgagcggc caggaggcca tctggcagcg ggtgtacctg gccttgggcc
 551    tgacccaggc agagatcaat gagttcttta ctggtcctgc cttcctggcc
 601    tggggcgaa tggcaacct gcacacctgg gatggcccc tgccccctc
 651    ctggcacatc aagcagcttt acctgcagca ccgggtcctg accagatgc
 701    gctccttcgg catgacccca gtgctgctg cattcgcggg gcatgttccc
 751    gaggctgtca ccagggtgtt ccctcaggtc aatgtcacga agatgggcag
 801    ttggggccac tttaactgtt cctactcctg ctccttcctt ctggctccgg
 851    aagacccat attccccatc atcgggagcc tcttcctgcg agagctgatc
 901    aaagagtttg cacagacca catctatggg gccgacactt tcaatgagat
 951    gcagccacct tcctcagagc cctcctacct tgccgcagcc accactgccg
1001    tctatgaggc catgactgca gtggatctg aggctgtgtg gctgctccaa
1051    ggctggctct tccagcacca gccgcagttc tggggcccg ccagatcag
1101    ggctgtgctg ggagctgtgc ccgtggccg cctcctggtt ctggacctgt
1151    ttgctgagag ccagcctgtg tataccgca ctgctcctt ccaggccag
1201    cccttcatct ggtgcatgct gcacaacttt ggggaaacc atggtctttt
1251    tggagcccta gaggctgtga cggaggccc agaagctgcc cgcctcttcc
1301    ccaactccac catggtaggc acgggcatgg ccccgagggg catcagccag
1351    aacgaagtgg tctattccct catggctgag ctgggctggc gaaaggaccc
1401    agtgccagat ttggcagcct gggtgaccag ctttgccgcc ggcggtatg
1451    gggtctccca cccggacgca ggggcagcgt ggaggctact gctccggagt
1501    gtgtacaact gctccgggga ggcctgcagg ggccacaatc gtagcccgct
1551    ggtcaggcgg ccgtccctac agatgaatac cagcatctgg tacaaccgat
1601    ctgatgtgtt tgaggctgg cggctgctgc tcacatctgc tcctccctg
1651    gccaccagcc ccgccttccg ctacgacctg ctggacctca ctcggcaggc
1701    agtgcaggag ctggtcagct tgtactatga ggaggcaaga agcgcctacc
1751    tgagcaagga gctggcctcc ctgttgaggg ctggaggcgt cctggcctat
1801    gagctgctgc cggcactgga cgaggtgctg gctagtgaca gccgcttctt
1851    gctgggcagc tggctagagc aggcccgagc agcggcagtc agtgaggccg
1901    aggccgattt ctacgagcag aacagccgct accagctgac cttgtggggg
1951    ccagaaggca acatcctgga ctatgccaac aagcagctgg cgggttggt
2001    ggccaactac tacccctc gctggcggct ttcctggag gcgctggttg
2051    acagtgtggc ccaggcatc cctttccaac agcaccagtt tgacaaaaat
2101    gtcttccaac tggagcaggc cttcgttctc agcaagcaga ggtaccccag
2151    ccagccgcga ggagacactg tggacctggc caagaagatc ttcctcaaat
2201    attacccccg ctgggtggcc ggctcttggt ga
```

(SEQ ID NO:2)

FIG. 2

N-ACETYL-ALPHA-D-GLUCOSAMINIDASE DEFICIENCY COMPOSITIONS AND METHODS

This application claims the benefit of U.S. Provisional Application Ser. No. 62/408,281 filed Oct. 14, 2016, and 62/455,905, filed Feb. 7, 2017, each of which is incorporated herein by reference in its entirety.

SEQUENCE LISTING

This application contains a Sequence Listing electronically submitted via EFS-Web to the United States Patent and Trademark Office as an ASCII text file entitled "535-0003_ST25.txt" having a size of 10 kilobytes and created on Sep. 25, 2017. The information contained in the Sequence Listing is incorporated by reference herein.

BACKGROUND

Mucopolysaccharidosis IIIB (MPS IIIB, also known Sanfilippo Syndrome B, N-acetyl-α-D-glucosaminidase deficiency, and NAGLU deficiency) is a genetic, progressive, systematic, rare and devastating autosomal recessive lysosomal storage disease (LSD) caused by a deficiency in N-acetyl-α-D-glucosaminidase (i.e., N-acetyl-alpha-D-glucosaminidase abbreviated as NAGLU). NAGLU is a lysosomal enzyme required for the degradation of heparan sulfate as part of the stepwise breakdown of glycosaminoglycans (GAG) in the lysosome. In patients with MPS IIIB, genetic mutations result in a marked decrease in NAGLU enzyme activity, which leads to the accumulation of heparan sulfate (HS) in the brain and other organs. The accumulation of HS leads to progressive brain atrophy, neurocognitive decline, behavioral disturbances, speech loss, increasing loss of mobility, and premature death. With over almost 200 different mutations identified to date MPS IIIB exhibits extensive molecular and genetic heterogeneity.

Approximately 1 out of 200,000 births is affected by MPS IIIB, and the deficiency mainly manifests in young children. MPS IIIB typically presents during the first few years of life, and patients have a greater than 50 percent mortality rate by 17 years of age. After initial symptom-free interval, patients suffering from MPS IIIB usually present with a slowing of mental development and behavioral problems, followed by progressive intellectual decline resulting in severe mental retardation, dementia and motor disease. Acquisition of speech is slow and incomplete. Profoundly affected patients may present delayed psychomotor and speech development as early as 2 years of age. The disease usually progresses to increasing behavioral disturbance and sleep disturbance. Although the clinical features are mainly neurological, patients often develop diarrhea, carious teeth, an enlarged liver and spleen, stiff joints, hirsteness and/or coarse hair and may exhibit blood-clotting problems. In the final stage of the illness, patients become immobile and unresponsive and develop swallowing difficulties and seizure. The life-span of an affected child typically does not extend beyond late teens to early twenties.

There are no approved treatments for patients with MPS IIIB. Current supportive care is palliative for behavioral problems, sleep disturbances, seizures, and other complications, and does not address the root cause of MPS IIIB or stop disease progression. However, investigational enzyme replacement therapy utilizing a recombinant human NAGLU (rhNAGLU) is currently being investigated in clinical trials for patients with MPS IIIB. The enzyme is a recombinant form of the N-acetyl-α-D-glucosaminidase (NAGLU) enzyme intended to replace the missing or deficient NAGLU enzyme, with the goal of to reduce accumulated HS. See WO2013/055888, published Apr. 18, 2013; US Pat. Appl. Publication 2013/0095092 (Quinn et al.), published Apr. 18, 2013. A recombinant human NAGLU preferably omits all or a portion of the signal peptide (amino acids 1-13) that is present in naturally occurring human NAGLU (SEQ ID NO:1).

SUMMARY OF THE INVENTION

In one aspect, the invention describes mutations in the nucleotide sequence of a human NAGLU gene that have been discovered to be associated with reduced N-acetyl-α-D-glucosaminidase (NAGLU) activity. These mutations may be referred to herein as "NAGLU activity-reducing mutations." In some embodiments, the activity of the NAGLU encoded by the mutated gene is reduced so far that it is no longer detectable or is eliminated. In other embodiments, the activity of the NAGLU encoded by the mutated gene is reduced but still detectable. In some embodiments, the NAGLU activity-reducing mutation is present in the coding region of a human NAGLU gene. A human NAGLU gene that is mutated such that it produces an NAGLU with reduced activity is suspected of being pathogenic and as such, is referred to herein as a potentially pathogenic NAGLU gene variant or allelic variant. In some embodiments, the mutation results in an amino acid substitution or deletion in the NAGLU encoded by the mutated NAGLU gene. In some embodiments, the mutation causes a truncation of NAGLU. The mutation can be, for example, a missense mutation or a nonsense mutation. In some embodiments, the mutation causes misregulation of precursor RNA splicing, and/or alternative precursor mRNA splicing. In some embodiments, the mutation can be an insertion or deletion of one or more amino acids, and optionally can cause a frameshift in the NAGLU encoded by the mutated NAGLU gene.

One or more of the NAGLU activity-reducing mutations described herein may occur alone, or in combination with each other and/or in combination with one or more known mutations in the human NAGLU gene.

In another aspect, the invention describes seven additional novel clinically identified mutations in the nucleotide sequence of a human NAGLU gene. A human NAGLU gene that includes one or more of these seven novel mutations is suspected of being pathogenic and as such, is also referred to herein as a potentially pathogenic NAGLU gene variant.

In another aspect, the invention provides a method for detecting the presence or absence of an NAGLU activity-reducing mutation in the nucleotide sequence of a NAGLU gene of a human subject. This method makes possible a determination as to whether the subject possesses a potentially pathogenic NAGLU gene variant, also referred to as a potentially pathogenic NAGLU allele or allelic variant. The presence of a potentially pathogenic gene variant may be indicative of MPS IIIB. Any convenient detection method can be used to detect an NAGLU activity-reducing mutation.

In another aspect, the invention provides a method for detecting the presence or absence of a novel clinically identified mutation, as described herein, in the nucleotide sequence of a NAGLU gene of a human subject. This method makes possible a determination as to whether the subject possesses a potentially pathogenic NAGLU gene variant, also referred to as a potentially pathogenic NAGLU allele or allelic variant. The presence of a potentially pathogenic gene variant may be indicative of MPS IIIB. Any convenient detection method can be used to detect a novel clinically identified mutation.

In another aspect, the invention provides a method for diagnosing Mucopolysaccharidosis IIIB (MPS IIIB, also known as Sanfilippo Syndrome B) in a human subject. The nucleotide sequence of the NAGLU gene of the subject, or related mRNA or cDNA, is analyzed to determine the presence of a mutation associated with reduced NAGLU activity, wherein reduced NAGLU activity of the gene variant is indicative MPS IIIB. Additionally or alternatively, the nucleotide sequence is analyzed to determine the presence of a novel clinically identified mutation, as described herein. Mutation detection can be used alone in combination with other diagnostic factors. The diagnostic method of the invention optionally includes treating the patient for MPS IIIB.

In some embodiments of the detection or diagnostic method, the NAGLU gene is present in or isolated from a biological sample obtained from a human subject. The subject can be a child or an adult. The polynucleotide evaluated for presence or absence of the mutation can be, for example, DNA, RNA or cDNA. In some embodiments of the detection or diagnostic method, genetic analysis for the presence or absence of a mutation takes the form of exomic or genomic analysis performed on nucleic acids obtained from the subject.

In another aspect, the invention provides a kit for detecting an NAGLU activity-reducing mutation and/or a novel clinically identified mutation in the nucleotide sequence of a NAGLU gene. In some embodiments, the kit includes at least one oligonucleotide primer specific for an NAGLU activity-reducing NAGLU gene mutation or a novel clinically identified NAGLU gene mutation as described herein, and instructions relating to detecting mutations in the nucleotide sequence of a NAGLU gene. In some embodiments, the kit includes at least one allele-specific oligonucleotide probe for an NAGLU activity-reducing NAGLU gene mutation or the novel clinically identified NAGLU gene mutation as described herein and instructions relating to detecting mutations in the nucleotide sequence of a NAGLU gene. Optionally the kit includes a multiplicity of primers or probes to permit the detection of a multiplicity of mutations in the nucleotide sequence of a human NAGLU gene, thereby increasing the diagnostic or screening efficiency of the kit.

In another aspect, the invention provides a method for treating a patient afflicted with, or suspected of being afflicted with MPS IIIB, wherein the nucleotide sequence of a NAGLU gene of the patient contains an NAGLU activity-reducing mutation and/or a novel clinically identified mutation as described herein. In some embodiments, the patient is treated with enzyme replacement therapy, for example by using recombinant NAGLU. In some embodiments, the patient is treated with therapeutic polynucleotides. Exemplary treatments and therapeutic agents for use with MPS IIIB patients are described, without limitation, in WO 2013/055888, published Apr. 18, 2013; US Pat. Appl. Publication 2013/0095092 (Quinn et al.), published Apr. 18, 2013; and WO 2016/054025, published Apr. 7, 2016.

Definitions

For convenience, certain terms employed in the specification, examples, and appended claims are set forth herein to illustrate and define the meaning and scope of the various terms used to describe the present invention.

"NAGLU" as used herein refers to "N-acetyl-α-D-glucosaminidase," and the two terms are used interchangeably throughout the specification. The NAGLU can be a human protein, i.e., human N-acetyl-α-D-glucosaminidase.

NAGLU is encoded by the NAGLU gene, which is present in the human population in a variety of allelic forms. The most prevalent allele, referred to herein as "wild-type" (WT), encodes a functional ("wild-type") NAGLU. Wild-type NAGLU is referred to herein as having "normal" activity. The amino acid sequence of a wild-type NAGLU (SEQ ID NO:1) is shown in FIG. 1, and the coding sequence of a wild-type human NAGLU gene (SEQ ID NO:2) is shown in FIG. 2. The x-ray crystallographic structure of human NAGLU protein is reported in U.S. Pat. No. 8,775,146. NAGLU catalyzes the hydrolysis of terminal non-reducing N-acetyl-D-glucosamine residues in N-acetyl-α-D-glucosaminides, which is referred to herein as "NAGLU activity." NAGLU activity is also known as NAG activity, α-acetylglucosaminidase activity, N-acetyl-α-glucosaminidase activity, α-N-acetylglucosaminidase activity, and N-acetyl-α-D-glucosaminidase activity according to the European Bioinformatics Institute (EMBL-EBI). "NAGLU activity" can be measured in vitro, for example, by the cleavage of the fluorogenic substrate, 4-methylumbelliferyl N-acetyl-α-D-glucosaminide (4MU-NAG). Cleavage of 4MU-NAG can be detected, for example, by excitation at about 360 nm and emission at 460 nm of the released fluorophore, 4-methylumbelliferone (4-MU). Results can be reported in relative fluorescence units (RFU). For example, the amount of substrate cleaved in a 30 minute endpoint assay can be quantified relative to a 4-MU standard curve, and one unit (U) of activity can be defined as the amount of enzyme required to cleave 1 micromole of 4MU-NAG per minute at 37° C. Accordingly, functional fragments or variants of NAGLU include fragments or variants that have NAGLU activity, e.g., the ability to hydrolyze terminal non-reducing N-acetyl-D-glucosamine residues in N-acetyl-α-D-glucosaminides.

As used herein "exogenous NAGLU" refers to NAGLU that is not naturally produced by a patient. For example, exogenous NAGLU includes recombinant NAGLU protein that is administered to a patient, NAGLU protein that is isolated from a person or animal and administered to a patient, and NAGLU protein that is produced (i.e., expressed) in a patient as a result of administration of NAGLU-encoding RNA and/or DNA or another treatment that increases expression of endogenous NAGLU protein.

As used herein an "NAGLU associated disease" is a disease or condition which is mediated by NAGLU activity or is associated with aberrant NAGLU expression or activity. An example of an NAGLU associated disease includes, but is not limited to, NAGLU deficiency such as Mucopolysaccharidosis type IIIB (also known as Sanflippo Syndrome B).

"Intravenous injection," often medically referred to as IV push or bolus injection, refers to a route of administration in which a syringe is connected to the IV access device and the medication is injected directly, typically rapidly and occasionally up to a period of 15 minutes if it might cause irritation of the vein or a too-rapid effect. Once a medicine has been injected into the fluid stream of the IV tubing, there must be some means of ensuring that it gets from the tubing to the patient. Usually this is accomplished by allowing the fluid stream to flow normally and thereby carry the medicine into the bloodstream. However, in some cases a second fluid injection, sometimes called a "flush," is used following the first injection to facilitate the entering of the medicine into the bloodstream.

"Intravenous infusion" refers to a route of administration in which medication is delivered over an extended period of time. For example, the medication can be delivered to a patient over a period of time between 1 and 8 hours. The medication can also be delivered to a patient over a period of about 1, about 2, about 3, about 4, about 5, about 6, about 7, or about 8 hours. To accomplish an intravenous infusion, an IV gravity drip or an IV pump can be used. IV infusion is typically used when a patient requires medications only at certain times and does not require additional intravenous fluids (e.g., water solutions which can contain sodium, chloride, glucose, or any combination thereof) such as those that restore electrolytes, blood sugar, and water loss.

The term "patient" as used herein refers to any person receiving or who has received or is to receive medical care or treatment, e.g., as directed by a medical care provider.

A "therapeutically effective" amount or a "therapeutically effective" dose, as the terms are used herein, refers to the amount or the dose (e.g., amount and/or interval) of drug required to produce an intended therapeutic response. A therapeutically effective dose refers to a dose that, as compared to a corresponding subject who has not received such a dose, results in improved treatment, healing, prevention, or amelioration of a disease, disorder, or side effect, or a decrease in the rate of the occurrence or advancement of a disease or disorder. The term also includes within its scope, doses effective to enhance physiological functions.

The terms "treat," "treating," and "treatment" refer to methods of alleviating, abating, or ameliorating a disease or symptom, preventing an additional symptom, ameliorating or preventing an underlying cause of a symptom, inhibiting a disease or condition, arresting the development of a disease or condition, relieving a disease or condition, causing regression of a disease or condition, relieving a condition caused by the disease or condition, or stopping a symptom of the disease or condition either prophylactically and/or after the symptom has occurred.

As used herein with reference to a particular dose, "$kg^{-1}$", "per kg", "/kg," and "per kilogram" represent "per kilogram of body weight" of the mammal, and thus the terms can be used interchangeably.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "proteins," "amino acid chains," or any other term used to refer to a chain or chains of two or more amino acids, are included within the definition of "polypeptide," and the term "polypeptide" may be used instead of, or interchangeably with any of these terms. The term "polypeptide" is also intended to be inclusive of the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

Other polypeptides disclosed herein are fragments, derivatives, analogs, or variants of the foregoing polypeptides, and any combination thereof. The terms "fragment," "variant," "derivative" and "analog" when referring to any of the polypeptides disclosed herein include any polypeptides which retain at least some of the activity of the corresponding native polypeptide (e.g., NAGLU polypeptide fragments, variants, derivatives, and analogs that retain the ability to hydrolyze terminal non-reducing N-acetyl-D-glucosamine residues in N-acetyl-α-D-glucosaminides). Fragments of polypeptides include, for example, proteolytic fragments, as well as deletion fragments. Variants of a polypeptide include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions, or additions. Derivatives are polypeptides which have been altered so as to exhibit additional features not found on the native polypeptide. Examples include fusion proteins. Variant polypeptides can also be referred to herein as "polypeptide analogs." As used herein, a "derivative" of a subject polypeptide can contain one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and/or ornithine can be substituted for lysine.

As used herein, the terms "glycan," "glycan structure," "glycan moiety," "oligosaccharide," "oligosaccharide structure," "glycosylation pattern," "glycosylation profile," and "glycosylation structure" have essentially the same meaning and each refers to one or more structures which are formed from sugar residues and are attached to glycosylated protein such as human NAGLU. For example, "N-glycan" or "N-linked glycan" refers to a glycan structure attached to a nitrogen of asparagine or arginine sidechain of the glycosylated protein. "O-glycan" or "O-linked glycan" refers to a glycan structure attached to the hydroxyl oxygen of serine, threonine, tyrosine, hydroxy lysine, or hydroxyproline side chain of the glycosylate protein.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. An "isolated" nucleic acid or polynucleotide is one that has been removed from its native environment. For example, a recombinant polynucleotide encoding NAGLU contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions. In addition, a vector, polynucleotide, or nucleic acid of the invention can encode heterologous coding regions, either fused or unfused to a nucleic acid encoding an NAGLU polypeptide or fragment, variant, or derivative thereof. Heterologous coding regions include without limitation specialized elements or motifs, such as a secretory signal peptide or a heterologous functional domain.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., the MEAVAVAAAVGVLLLAGAGGAAG (SEQ ID NO:3) signal peptide of human NAGLU is used, or a functional derivative of that sequence that retains the ability to direct the secretion of the polypeptide that is operably associated with it. Alternatively, a heterologous signal peptide (e.g., a heterologous mammalian or avian signal peptide), or a functional derivative thereof, may be used. For example, the wild-type leader sequence may be substituted with the leader sequence of human tissue plasminogen activator (TPA) or mouse β-glucuronidase.

"Vector" means a polynucleotide comprised of single strand, double strand, circular, or supercoiled DNA or RNA. A typical vector can be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements can be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally can be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest can be desirable to achieve this end. For example, in some cases it can be necessary to modify the sequence so that it can be attached to the control sequences with the appropriate orientation, or to maintain the reading frame. The control sequences and other regulatory sequences can be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, "host cells" refers to cells that harbor vectors constructed using recombinant DNA techniques and encoding at least one heterologous gene.

As used herein, the term "pharmaceutical composition" refers to a mixture of a compound described herein with other chemical components, such as carriers, stabilizers, diluents, dispersing agents, suspending agents, thickening agents, and/or excipients.

The words "preferred" and "preferably" refer to embodiments of the invention that may afford certain benefits, under certain circumstances. However, other embodiments may also be preferred, under the same or other circumstances, whether described as such or not herein. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The above summary of the invention is not intended to describe each disclosed embodiment or every implementation of the invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

DESCRIPTION OF THE FIGURES

FIG. 1 depicts the amino acid sequence of wild-type human N-acetyl-α-D-glucosaminidase (NAGLU) (SEQ ID NO:1). Amino acid residues 1-23 represent a signal peptide. See UniProtKB P54802 ANAG_Human.

FIG. 2 depicts cDNA of wild-type human NAGLU (SEQ ID NO:2).

ILLUSTRATIVE DESCRIPTION OF THE INVENTION

Figure 3:
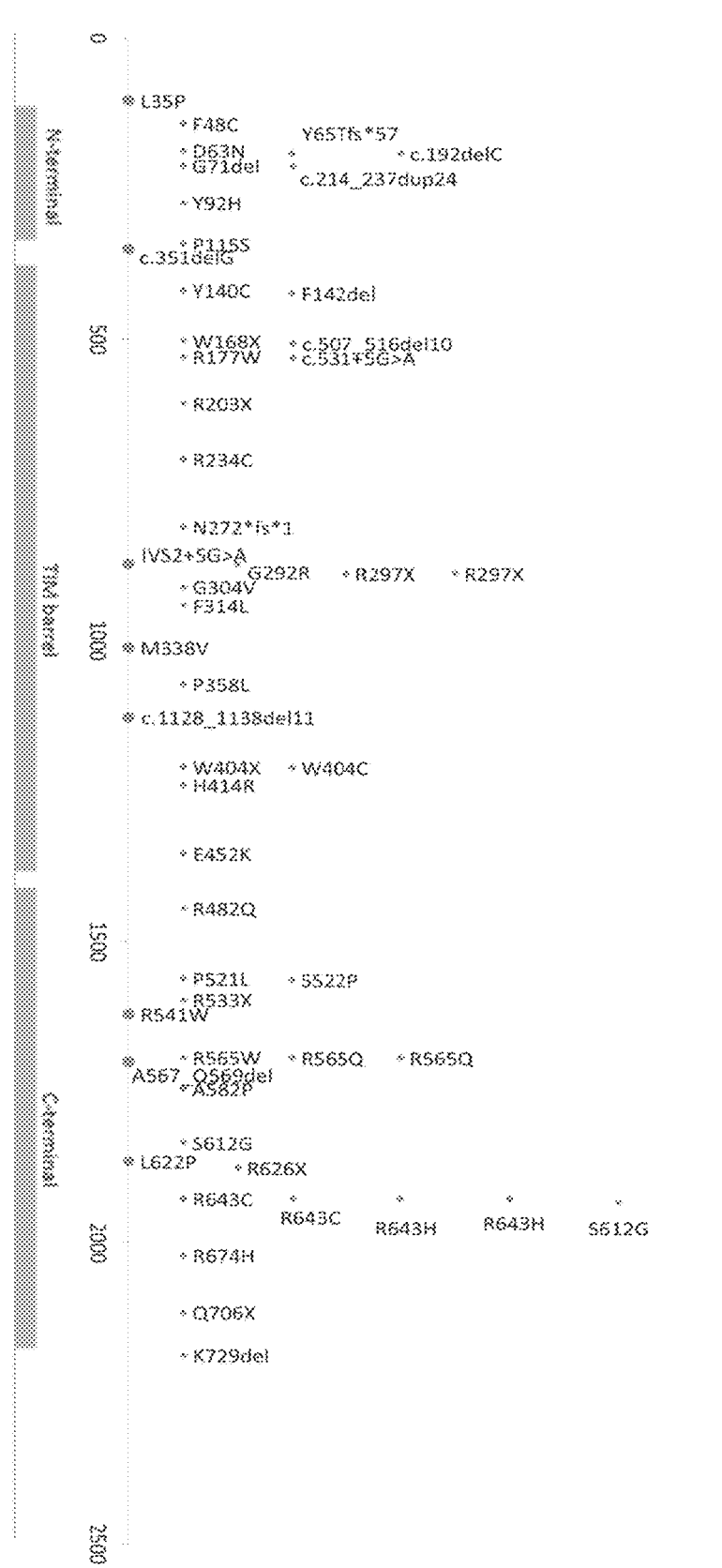
FIG. 3 depicts the location of mutations for NAGLU variants on a NAGLU protein. Mutation positions for the eight novel variants are marked by red dots. Bars show the three conserved domains in NAGLU: N-terminal domain, TIM barrel domain, and C-terminal domain.

This disclosure describes mutations in the nucleotide sequence of a human NAGLU gene that may be associated with reduced N-acetyl-α-D-glucosaminidase (NAGLU) activity. NAGLU activity-reducing mutations are of clinical and research interest because reduced NAGLU activity is a marker for MPS IIIB. It is expected that the identification of NAGLU activity-reducing mutations in the human NAGLU gene as set forth herein will be of important medical significance in that it will improve genetic screening for human subjects suspected of having MPS TIM.

In one aspect, the invention provides a method for detecting a potentially pathogenic mutation in a human NAGLU nucleotide sequence. The detection method includes providing a biological sample that includes a nucleic acid; and performing a genetic analysis on the biological sample to detect the presence of a potentially pathogenic mutation in a human NAGLU nucleotide sequence. Optionally, the detection method includes diagnosing a patient with MPS IIIB when the presence of a potentially pathogenic mutation in the NAGLU nucleotide sequence of the patient is detected. The method may further include administering a therapeutically effective amount of a recombinant human NAGLU to the patient. An exemplary recombinant human NAGLU that can be administered to a patient is described in WO2013/055888 and US 2013/0095092.

In another aspect, the invention provides a method for diagnosing MPS IIIB in a patient. The diagnostic method includes providing a biological sample from a patient, wherein the sample includes a nucleic acid; performing a genetic analysis on the biological sample to detect the presence of a potentially pathogenic mutation in a human NAGLU nucleotide sequence; and diagnosing the patient with MPS IIIB when the presence of a potentially pathogenic mutation in the NAGLU nucleotide sequence of the subject is detected. The method may further include administering a therapeutically effective amount of a recombinant human NAGLU to the patient.

In another aspect, the invention provides a method for treating a patient afflicted with or suspected of being afflicted with MPS IIIB. The method includes administering a therapeutically effective amount of a recombinant human NAGLU to the patient who has been determined to possess at least one NAGLU allelic variant that includes a potentially pathogenic mutation as described herein. Both NAGLU alleles of the patient may have pathogenic mutations; in other words, the patient may have biallelic pathogenic variants in the NAGLU gene.

The potentially pathogenic mutation can include, for example, a nucleotide sequence mutation encoding an amino acid substitution at amino acid position L35, M338, R541, and/or L622 relative to the wild-type human NAGLU amino acid sequence (SEQ ID NO:1), and/or, for example, a nucleotide substitution or in frame deletion such as c.104T>C, c.1012A>G, c.1621C>T, c.1865T>C, or c.1700_1708del9 relative to the wild-type human NAGLU cDNA sequence (SEQ ID NO:2), where "c." designates numbering according to the coding sequence. Alternatively or additionally, the potentially pathogenic mutation can include one or more mutations that affect precursor mRNA splicing, and/or that cause a frame shift or truncation, such as c.1128_1138del11, c.351delG, and IVS2+5G>A relative to the wild-type human NAGLU cDNA sequence (SEQ ID NO:2). In some embodiments, the mutation is a NAGLU activity-reducing mutation.

In one embodiment, a potentially pathogenic mutation in the NAGLU gene is identified by analyzing a biological sample obtained from a patient known to be afflicted with, or suspected of being afflicted with, MPS IIIB. NAGLU gene variants that include one or more potentially pathogenic mutations can be clinically identified by performing genetic analysis on a biological sample obtained from a such a patient, where the biological sample to be analyzed contains a nucleic acid, for example genomic DNA or RNA. Illustrative examples of novel, clinically identified potentially pathogenic mutations in the NAGLU gene are set forth in Example I. Clinically identified mutations are of particular clinical and research interest because they are discovered in patients who have been diagnosed with (or are suspected of having) MPS IIIB. It is expected that the identification of these mutations in the nucleotide sequence of a human NAGLU gene will be of important medical significance in that it will improve genetic screening for human subjects suspected of having MPS IIIB.

Genetic analysis of a biological sample can be performed, for example, using whole transcriptome sequencing, whole exome sequencing, whole genome sequencing, or hybridization to a DNA microarray, as described further elsewhere herein. In methods that involve the use of a biological sample, the biological sample can be obtained from a pediatric or adult patient.

It should be understood that mutations in the NAGLU gene of a patient, including pathogenic mutations and potentially pathogenic mutations, can be present in one or both NAGLU alleles of the patient. Pathogenic mutations may be present in both alleles of a patient diagnosed with MPS TIM, as MPS TIM is an autosomal recessive disorder. In other words, the patient may have biallelic pathogenic variants of the NAGLU gene A NAGLU allele of a patient may contain one or more pathogenic or potentially pathogenic mutations, which mutations may be the same as or different from the mutations, if any, present in the other NAGLU allele.

In another embodiment, a potentially pathogenic mutation in the NAGLU gene is identified by analyzing NAGLU nucleotide or amino acid sequence data available from various protein or nucleic acid databases. As shown in Table 2, over 200 NAGLU gene variants are known. The coding region of a NAGLU gene variant described in a database can be genetically engineered into a cellular or acellular expression system, and the expressed protein can be assayed for enzymatic activity, for example using an in vitro enzyme assay, as described in more detail elsewhere herein and as exemplified in Example II. A cellular assay can be used, although an in vitro assay is preferred. The method permits evaluation of any known human NAGLU nucleotide sequence, such as those variants cataloged in the Exome Aggregation Consortium (ExAC) database, for potential pathogenicity. As explained in more detail elsewhere herein, NAGLU gene variants identified in this manner may be considered potentially pathogenic if the enzyme encoded by the NAGLU gene variant exhibits reduced NAGLU activity.

The invention further provides a method of screening for presence of MPS IIIB in a patient. The method includes determining the nucleotide sequence of one or more of the patient's NAGLU alleles; and determining whether one or more of the patient's NAGLU alleles includes a potentially pathogenic mutation as described herein. Optionally, the screening method includes screening for the presence of additional disease in the patient; for example, the screening method can include screening for one or more additional Mendelian disorders.

In another aspect, the invention provides a kit for detecting a potentially pathogenic mutation in a human NAGLU nucleotide sequence. In one embodiment, the kit includes at least one oligonucleotide primer specific for a potentially pathogenic mutation as described herein, and optionally, instructions relating to detecting mutations in the NAGLU nucleotide sequence. In another embodiment, the kit includes at least one allele-specific oligonucleotide probe for a potentially pathogenic mutation as described herein, and instructions relating to detecting mutations in the NAGLU nucleotide sequence.

In another aspect, the invention provides an isolated polynucleotide that includes a mutated human NAGLU nucleotide sequence having a mutation selected from the group consisting of c.104T>C, c.1012A>G, c.1621C>T, c.1865T>C, c.1128_1138del11, c.351delG, IVS2+5G>A, and c.1700_1708del9 relative to the wild-type NAGLU nucleotide coding sequence (SEQ ID NO:2), as well as a vector operably encoding the polynucleotide, and a host cell that includes the vector. Methods of making and using the polynucleotide, vector and host cell are also encompassed by the invention.

Reduction in NAGLU Activity

NAGLU is enzyme that has N-acetyl-α-D-glucosaminidase activity. "Reduced NAGLU activity" is defined in relation to the N-acetyl-α-D-glucosaminidase activity of wild-type human NAGLU. The activity of the gene products by NAGLU variants can be measured in an assay that supplies 4-methylumbelliferyl N-acetyl-α-D-glucosaminide (4MU-NAG) as a substrate, and detects the production of the cleaved fluorophore 4-methylumbelliferyl at excitation/emission wavelengths of 360/460+/−40 nm. A representative activity assay is described in Example II. In the cell lysate assay described in Example II, a NAGLU gene product can be considered as having "reduced NAGLU activity" if, for example, it exhibits less activity than of wild-type NAGLU activity. In an assay of cell culture supernatant described in Example II, a NALGU gene product is considered as having "reduced NAGLU activity" if, for example, it exhibits significantly less activity than of wild-type NAGLU activity. Cutoff values can be used to determine reduced NAGLU activity. Exemplary cutoff values for cell lysate activity of 1%, 2%, 5%, 7% 10%, 12% 15%, 20%, 25%, 30%, 35%, 40%, 45%, 50%, 55%, 60%, 65%, 70%, 75%, 80%, 85% or higher, or any value in between, can be used to identify allelic variants having "reduced NAGLU activity." Likewise, an exemplary cutoff value for supernatant activity of 0.1%, 0.2%, 0.5%, 0.7% 1.0%, 1.2% 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 10%, 12%, 15%, 20%, 25%, 30%, 35%, 40% or higher, or any value in between, can be used to identify allelic variants having "reduced NAGLU activity." The invention is not limited by the activity assay used, and other activity assays can be employed. See, e.g., Mauri et al., PLoS One, (2013) 8(6):e60860; Marsh et al., Clinical Genetics (1985) 27: 258-262; Chow et al., Carbohydrate Research (1981) 96:87-93; Weber et al., Protein Expression and Purification, (2001)21:251-259); WO2013/055888. Allelic variants that exhibited reduced NAGLU activity are characterized herein as possessing "NAGLU activity-reducing" mutations. The characteristic of "reduced NAGLU activity" is used to identify mutant NAGLU gene products that may be considered potentially pathogenic NAGLU variants and thereby indicative of or associated with MPS TIM.

It should be understood that NAGLU gene products exhibiting "reduced NAGLU activity" include those gene products having no detectable NAGLU activity. Gene products having no detectable NAGLU activity may have activity at too low a level to be detected, or they may have no activity at all (i.e., activity has been eliminated).

NAGLU Activity-Reducing Mutations

FIG. 1 shows the amino acid sequence of wild-type (normal) human NAGLU (SEQ ID NO:1). FIG. 2 shows a sequence of the coding region of the wild-type (normal) human NAGLU gene (SEQ ID NO:2). The newly identified NAGLU activity-reducing mutations are described with reference to the human NAGLU wild-type (normal) sequence. It should be understood that one or more of the NAGLU activity-reducing mutations described herein may occur alone, together, and/or in combination with one or more known mutations in the human NAGLU gene.

A mutation in the nucleotide sequence of the human NAGLU gene can, in some embodiments, result in an amino acid substitution in the NAGLU encoded by the mutated NAGLU gene. In some embodiments, the mutation causes a truncation of NAGLU. The mutation can be, for example, a missense mutation or a nonsense mutation. In some embodiments, the mutation causes misregulation of precursor RNA splicing, and/or alternative precursor mRNA splicing. In some embodiments, the mutation can include an insertion or deletion and may or may not cause a frameshift in the NAGLU encoded by the mutated NAGLU gene. A mutation can occur in an exon or an intron; a mutation in an intron may not alter the NAGLU coding sequence, but may, for example, affect splicing. Potentially pathogenic gene variants may therefore include single base, site specific, or other types of nucleotide sequence mutations.

In some embodiments, a mutation in the nucleotide sequence of the human NAGLU gene can occur in a region that encodes a NAGLU protein domain, such as an N-terminal domain, a TIM barrel domain, and/or a C-terminal domain. Potentially pathogenic NAGLU gene variants can include variants having mutations in or affecting one or more NAGLU protein domain, including but not limited to an N-terminal domain, a TIM barrel domain, a C-terminal domain, or any combination thereof, including one or more mutations that span or affect more than one protein domain.

In some embodiments, NAGLU activity-reducing mutations in a NAGLU gene include amino acid substitutions or in frame deletions at one or more of the amino acid positions in the encoded NAGLU gene product as shown in Table 1 and/or in Table 2. Exemplary mutations producing potentially pathogenic gene variants can include amino acid substitutions at one or more of positions L35, M338, R541, or L622, or in frame deletion at A567_Q569del, as numbered for human wild-type NAGLU in FIG. 1, and/or any of the positions shown in Table 1 and/or Table 2.

When screening a subject's DNA or RNA for possible pathogenic NAGLU allelic variants according to the method of the invention, one of skill in the art can readily determine by inspecting SEQ ID NO:2 (the wild-type human cDNA sequence for NAGLU) which nucleotide base changes relative to the wild-type cDNA sequence will yield amino acid substitutions. Nucleotide changes that will generate an amino acid substitution at a particular position can be determined with reference to the codon encoding the amino acid at that position in the normal NAGLU sequence, and there are only a limited number of possibilities permitted by the genetic code. Exemplary amino acid substitutions or in frame deletions yielding a potentially pathogenic mutant NAGLU are shown in Table 1 and/or Table 2 and/or include the following: L35P, M338V, R541W, L622P, and A567_Q569del.

In some embodiments, NAGLU activity-reducing mutations in a NAGLU gene include mutations that affect precursor mRNA splicing, and/or that include frame shift mutations or truncations. Exemplary mutations producing potentially pathogenic gene variants can include frameshifts or splicing variants such as such c.1128_1138del11, c.351delG, and IVS2+5G>A, and/or other mutations shown in Table 1 and/or Table 2.

TABLE 1

Clinically identified pathogenic mutations

| Mutation | Amino Acid Position* | Exemplary Amino Acid Mutation |
|---|---|---|
| c.104T > C | L35 | L35P |
| c.1012A > G | M338 | M338V |
| c.1621C > T | R541 | R541W |
| c.1865T > C | L622 | L622P |
| c.1128_1138del11 | (frameshift) | |

TABLE 1-continued

Clinically identified pathogenic mutations

| Mutation | Amino Acid Position* | Exemplary Amino Acid Mutation |
|---|---|---|
| c.351delG | (frameshift) | |
| IVS2 + 5G > A | (splice variant) | |
| c.1700_1708del9 | (in frame deletion) | A567_Q569del |

*Position as specified in wild-type human NAGLU (SEQ ID NO: 1)

The newly identified NAGLU activity-reducing mutations identified herein can occur alone or in combination with each other or with one or more known pathogenic mutations in the nucleotide sequence of the human NAGLU gene. Exemplary known amino acid substitutions resulting in pathogenic allelic variants are included in Table 2. Exemplary known frame shift mutations resulting in pathogenic allelic variants are also included in Table 2. Table 2 also includes mutation information for allelic NAGLU variants that have not yet been analyzed for pathogenicity, but can be analyzed in accordance with the method described herein for assaying NAGLU activity in vitro and determining potential pathogenicity. Table 2 also includes some of the newly identified pathogenic mutations identified in Example I.

In Silico Analysis

In some embodiments, the potential pathogenicity of a NAGLU gene variant can be evaluated using in silico techniques. One or more in silico prediction methods, such as MutationTaster, PolyPhen2, SIFT, and/or Provean, are utilized to assess the severity of missense mutations and to predict the impact of the mutation on NAGLU enzymatic activity. Missense mutations can be identified based on a unanimous score, or on a consensus score, of two, three, four or more in silico methods. For example, a mutation can be identified as "deleterious" if four methods predict it to be "deleterious."

NAGLU Gene Variant Detection

The invention includes a method for detecting the presence or absence of an NAGLU activity-reducing mutation or a novel clinically identified mutation in the nucleotide sequence of a NAGLU gene of a human subject. Any one or more of the NAGLU activity-reducing mutations or the novel clinically identified mutations described herein can be detected. The presence of one or more NAGLU alleles possessing an NAGLU activity-reducing mutation or clinically identified mutation as described herein (i.e., one or more potentially pathogenic NAGLU gene variants) has clinical relevance to the diagnosis of MPS IIIB.

Detection of a mutation in the nucleotide sequence of a NAGLU gene can be accomplished using any convenient method. Many techniques for genetic testing and genetic analysis are known to the art. Genetic analysis for the presence of a potentially pathogenic NAGLU gene variant in a subject can be carried out, for example, using recently developed nucleotide sequencing technologies or using traditional hybridization technologies. For example, the analysis can be carried out using positional cloning based on linkage analysis and/or Sanger sequencing. Another option is RNA whole transcriptome sequencing, which may also be referred to as RNA sequencing, RNA-seq or whole transcriptome shotgun sequencing (WTSS), which typically utilizes next-generation sequencing technologies (NGS) and focuses on a gene expression profile, is able to detect alternative splicing events, and can detect single nucleotide variants. Another option is exome sequencing or whole exome sequencing (WES or WXS), wherein some or all of the expressed genes in a genome (i.e., the exome) are sequenced. Whole-exome sequencing facilitates identification of autosomal recessive disease genes in single patients from non-consanguineous families. Another option is whole-genome sequencing (WGS) which provides a complete view of the human genome, including point mutations in distant enhancers and other regulatory elements. Pabinger et al., Brief. Bioinform (2014) 15(2):256-278, Epub Jan. 21, 2013. Other exemplary methods of genetic analysis include, but are not limited to, restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. It should be understood that mutation analysis and detection techniques are rapidly evolving and detection of a potentially pathogenic NAGLU gene variant is not limited to any particular detection technique.

Mutations in the nucleotide sequence of a NAGLU gene can be detected by analyzing any polynucleotide or polynucleotide fragment that derives from, directly or indirectly the NAGLU gene of a subject. Types of polynucleotides that can be analyzed for mutations include, without limitation, genomic DNA (whole or partial), exomic RNA (whole or partial), primary RNA transcripts such as precursor RNA, processed RNA such as spliced mRNA, mature RNA and mRNA, and cDNA. The nucleotide sequence to be analyzed typically includes coding sequences, for example exon sequences, and may also include intron sequences, particularly intron sequences that proximal to splice junctions and may thus affect production of the mature mRNA and/or protein translation and structure.

The nucleic acids (e.g., DNA or RNA) to be analyzed for presence of one or more NAGLU activity-reducing and/or novel clinically identified gene mutations can be present in or isolated from a biological sample obtained from the subject. The biological sample can be a tissue sample or a fluid sample, for example. The subject can be a child or an adult. Nucleic acids may be fragmented into smaller constituent polynucleotides, prior to analysis.

Advantageously, if the detection method yields a positive result, in that one or more of the specified pathogenic NAGLU allelic variants is detected in a subject, genetic testing can then be performed on blood relatives in order to determine whether other family members possess the potentially pathogenic NAGLU allelic variants.

Diagnostic Methods

Detection of a potentially pathogenic NAGLU gene variant in a human subject can aid in making, or can confirm, a diagnosis of MPS MB in the subject. Lysosomal storage diseases that can be diagnosed using the diagnostic method of the invention include MPS IIIB. The nucleotide sequence of NAGLU gene of the subject, or associated mRNA or cDNA, is analyzed as in the detection method in order to determine the presence of a mutation associated with reduced NAGLU activity, wherein reduced NAGLU activity of the gene variant is consistent with or indicative of MPS IIIB, and or a clinically identified mutation in the nucleotide sequence of a NAGLU gene as described herein. Optionally, the diagnostic method includes determining whether other signs or symptoms associated with MPS IIIB are present in the subject. This determination can be made before or after genetic analysis to determine whether the subject carries a potentially pathogenic NAGLU gene variant. The diagnostic method of the invention, involving the detection of genetic mutations, can also optionally be performed in combination with or as an adjunct to, either before or after, one or more assays for deficient NAGLU enzyme activity in peripheral blood leukocytes, fibroblasts, or dried blood spots. Thus, the diagnostic method of the invention optionally further includes measuring NAGLU activity in the subject. The level of NAGLU activity in a patient prior to treatment can be about 1%, about 2%, about 3%, about 5%, about 10%, about 15%, about 20%, about 30%, about 40%, about 50%, about 60%, about 70%, or about 80% of normal levels of NAGLU activity. For example, the level of NAGLU activity in a patient prior to treatment can be about 50% or less of normal levels of NAGLU activity, or about 40% or less of normal levels of NAGLU activity, or about 30% or less of normal levels of NAGLU activity, or about 20% or less of normal levels of NAGLU activity, or about 10% or less of normal levels of NAGLU activity, or about 5% or less of normal levels of NAGLU activity. Some patients show no measurable NAGLU activity prior to treatment. The level of NAGLU activity in a patient can be measured in cultured fibroblasts or lymphocytes (e.g., leukocytes) obtained from a human patient suffering from NAGLU deficiency. Lymphocytes include, but are not limited to, peripheral blood mononuclear cells (PMBC). Enzymatic activity can be measured using methods known in the art, for example according to the methods described in Mauri et al., PLoS One, (2013) 8(6):e60860; Marsh et al., Clinical Genetics (1985) 27: 258-262, Chow et al., Carbohydrate Research (1981) 96:87-93; and Weber et al., Protein Expression and Purification, (2001)21:251-259).

The diagnostic method can be performed on a subject suspected of having MPS IIIB, or as a component of a more general genetic screen. For example, a subject can be screened for the presence of a potentially pathogenic NAGLU allelic variant in combination with screening for pathogenic gene variants associated with other Mendelian disorders such as phenylketonuria, cystic fibrosis, sickle-cell anemia, oculocutaneous albinism, Huntington's disease, myotonic dystrophy, hypercholesterolemia, neurofibromatosis, polycystic kidney disease, hemophilia, Duchenne's muscular dystrophy, Rett's syndrome, or other Mendelian diseases (see the National Center for Biotechnology Information (NCBI) databases Online Mendelian Inheritance in Man, http://www.ncbi.nlm.nih.gov/omim, and Clin-Var, http://www.ncbi.nlm.nih.gov/omim; see also Chial et al., Nature Education 1(1):192 (2008)).

The diagnostic method of the invention optionally includes treating the patient for MPS IIIB.

Treatment Methods

The invention also includes treating a patient who has been found to carry a potentially pathogenic NAGLU variant as described herein. Such a patient is either afflicted with, or suspected of being afflicted with MPS IIIB. In some embodiments, the patient is treated with enzyme replacement therapy using an exogenous NAGLU, for example by using recombinant human NAGLU (rhNAGLU). A patient who has been found to carry a potentially pathogenic NAGLU variant can be treated by administering a therapeutically effective amount of exogenous NAGLU. The exogenous NAGLU can be a recombinant human NAGLU such as described in WO2013/055888 and US 2013/0095092, and may have an N-linked glycan structure that includes at least one mannose and/or mannose-6-phosphate.

The method for treating a patient who has been found to carry a potentially pathogenic NAGLU variant can include can include single or multiple administrations of a therapeutically effective amount of exogenous NAGLU. Exogenous NAGLU can be administered at regular intervals, depending on the nature, severity and extent of the subject's condition. In some embodiments, a therapeutically effective amount of exogenous NAGLU may be administered intravenously or intrathecally, periodically at regular intervals, e.g., once every year, once every six months, once every five months, once every three months, bimonthly (once every two months), monthly (once every month), biweekly (once every two weeks), weekly, or more frequently, such as every day or every other day. The exogenous NAGLU may be effectively internalized into human cells, and may cause an increase in NAGLU activity in the patient. An increase in NAGLU activity can be measured, for example, in vitro or in human cells such as lymphocytes and/or fibroblasts as described herein and elsewhere, such as in WO2013/055888 and US 2013/0095092.

In one embodiment, exogenous NAGLU is administered intravenously to the subject at a dosage of about 0.5 to about 50 mg/kg body weight. In another embodiment, exogenous NAGLU is administered intravenously to the subject at a dosage of about 1 to about 30 mg/kg body weight. In another embodiment, exogenous NAGLU is administered intravenously to the subject at a dosage of about 6 to about 27 mg/kg body weight.

In one embodiment, an effective amount of exogenous NAGLU is administered intravenously to a subject in need thereof every other week (QOW). In some aspects, the method includes administering a dose of about 0.3 mg/kg to about 10 mg/kg of exogenous NAGLU every other week. For example, a dose of about 0.3 mg/kg, about 1 mg/kg, about 3 mg/kg, about 5 mg/kg, about 6 mg/kg, about 7 mg/kg, about 8 mg/kg, about 9 mg/kg, or about 10 mg/kg, can be administered every other week. Preferably, the intravenous administration is by intravenous infusion, such as a two hour intravenous infusion.

In some embodiments, exogenous NAGLU is administered by infusion, and the infusion can occur over an extended time period, for example, 30 minutes to 10 hours. Thus, the infusion can occur, for example, over a period of about 1 hour, about 2 hours, about 3 hours, about 4 hours, or about 5 hours. The infusion can also occur at various rates. Thus, for example, the infusion rate can be about 1 mL per hour to about 20 mL per hour. In some embodiments, the infusion rate is 5 mL to 10 mL per hour. In one embodiment, the infusion rate is 1, 2, 3, 4, 5, 6, 7, 8, 9, 10, 11, 12, 13, 14, 15, 16, 17, 18, 19 or 20 mL per hour. In one embodiment, the infusion rate is 0.1 to 5 mg/kg/hr. In one embodiment, the infusion rate is about 0.1, about 0.2, about 0.3, about 0.5, about 1.0, about 1.5, about 2.0, about 3.0, or about 4.0 mg/kg/hr. Ranges and values intermediate to the above recited ranges and values are also contemplated to be part of the invention.

In one embodiment, exogenous NAGLU is administered intravenously by IV infusion by any useful method. In one example, exogenous NAGLU can be administered by intravenous infusion through a peripheral line. In another example, exogenous NAGLU can be administered by intravenous infusion through a peripherally inserted central catheter. In another example, exogenous NAGLU can be administered by intravenous infusion facilitated by an ambulatory infusion machine attached to a venous vascular access port. In one embodiment of intravenous infusion, the medication is administered over a period of 1 to 8 hours depending on the amount of medication to be infused and the patient's previous infusion-related reaction history, as determined by a physician skilled in the art. In another embodiment, exogenous NAGLU is administered intravenously by IV injection.

In another embodiment, exogenous NAGLU can be administered via intraperitoneal or intrathecal injection.

In another embodiment, exogenous NAGLU is intrathecally administered to the subject. In one embodiment, the exogenous NAGLU is intrathecally administered at a dosage of at least about 0.3, 0.4, 0.5, 0.6, 0.7, 0.8, or 0.9 mg/kg body weight. In another embodiment, exogenous NAGLU is intrathecally administered at a dosage of about 1, 2, 3, 4, 5, 6, 7, 8, 9, or 10 mg/kg body weight. In another embodiment, exogenous NAGLU is administered intrathecally at a dosage of about 10 to about 30 mg/kg body weight.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg bra body in weight. Ranges and values intermediate to the above recited ranges and values (e.g., 10-50 mg/kg, 1-5 mg/kg, 2-8 mg/kg, 5-10 mg/kg, 0.1-10 mg/kg, 0.3-30 mg/kg, 0.3-50 mg/kg, 0.5-10 mg/kg, 5-30 mg/kg, or 6-27 mg/kg) are also contemplated to be part of the invention.

In some embodiments, the therapeutically effective dose is greater than or at least about 0.1 mg/kg body weight, greater than or at least about 0.2 mg/kg body weight, greater than or at least about 0.3 mg/kg body weight, greater than or at least about 0.4 mg/kg body weight, greater than or at least about 0.5 mg/kg body weight, greater than or at least about 1.0 mg/kg body weight, greater than or at least about 3 mg/kg body weight, greater than or at least about 5 mg/kg body weight, greater than or at least about 6 mg/kg body weight, greater than or at least about 7 mg/kg body weight greater than or at least about 10 mg/kg body weight, greater than or at least about 15 mg/kg body weight, greater than or at least about 20 mg/kg body weight, greater than or at least about 30 mg/kg body weight, greater than or at least about 40 mg/kg body weight, greater than or at least about 50 mg/kg body weight, greater than or at least about 60 mg/kg body weight, greater than or at least about 70 mg/kg body weight, greater than about or at least 80 mg/kg body weight, greater than or at least about 90 mg/kg body weight, greater than or at least about 100 mg/kg body weight. Ranges and values intermediate to the above recited ranges and values are also contemplated to be part of the invention.

In some embodiments, the therapeutically effective dose may also be defined by mg/kg brain weight. As one skilled in the art would appreciate, the brain weights and body weights can be correlated (see, e.g., Dekaban A S. "Changes in brain weights during the span of human life: relation of brain weights to body heights and body weights," Ann Neurol 1978; 4:345-56).

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5: 10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Exemplary administration and dosing protocols, as well as suitable pharmaceutical compositions, are exemplified in WO2013/055888, U.S. Pat. Pub. US2013/0095092, and WO/2016/054025. For example, WO/2016/054025 describes methods for the initial dosing regimen and subsequent maintenance of therapeutic levels of exogenous NAGLU in the central nervous system (e.g., brain tissue) in a mammal undergoing long-term enzyme replacement therapy with diseases associated with NAGLU deficiency, e.g., MPS IIIB, using intravenous administration of exogenous NAGLU. Enzyme replacement dosing regimens identified for treating lysosomal acid lipase deficiency (see, e.g., U.S. Pat. No. 8,663,631, WO2012/050695, U.S. Pat. Pub. US20130209436, and WO2011/133960) may also be applicable to enzyme replacement therapy utilizing exogenous NAGLU.

Other treatment methods include the administration of therapeutic polynucleotides analogous to the methods described in US2014/0155475 for treatment of lysosomal acid lipase deficiency.

Optionally, the patient is treated with a second therapeutic. The second therapeutic can include, for example, a cholesterol-reducing drug (e.g., statin or ezetimibe), an antihistamine (e.g., diphenhydramine), or an immunosuppressant. Nonlimiting examples of antihistamines include antihistamines include, without limitation, clemastine, doxylamine, loratidine, desloratidine, fexofenadine, pheniramine, cetirizine, ebastine, promethazine, chlorpheniramine, levocetirizine, olopatadine, quetiapine, meclizine, dimenhydrinate, embramine, dimethidene, and dexchloropheniramine. Nonlimiting examples of immunosuppressants include antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept) and anti-OX-40 antibodies.

Nonlimiting examples of cholesterol-reducing drugs include examples of such agents include: atorvastatin (Lipitor® and Torvast®, fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®), and simvastatin (Zocor®, Lipex®). Suitable second therapeutics are also described in WO2013/055888, US2013/0095092, and WO/2016/054025.

Expression of Variant NAGLU Nucleotide Sequences

As will be appreciated by a person of skill in the art, a nucleotide sequence encoding an NAGLU can be introduced into and optionally expressed in a host cell, and the invention encompasses methods for introducing NAGLU-encoding nucleotide sequences into host cells and optionally expressing them. Introducing a potentially pathogenic NAGLU gene variant nucleotide sequence into a host cell and optionally expressing a NAGLU encoded by the variant can be achieved through any of a number of molecular biology techniques. Typically, the polynucleotide encoding the NAGLU is introduced into the cell using a vector. The vector can be a cloning vector, a shuttle vector, or an expression vector, depending on the intended purpose. The polynucleotide may be circular or linear, single-stranded or double stranded, and can be DNA, RNA, or any modification or combination thereof. The vector can be any molecule that may be used as a vehicle to transfer genetic material into a host cell. Examples of vectors include plasmids, viral vectors, cosmids, and artificial chromosomes, without limitation. Examples of molecular biology techniques used to transfer nucleotide sequences into a microorganism include, without limitation, transfection, electroporation, infection, transduction, and transformation. These methods are routine and known in the art. Insertion of a vector into a target cell is usually called transformation for bacterial cells and transfection for eukaryotic cells, however insertion of a viral vector is often called transduction. The terms transformation, transfection, infection, and transduction, for the purpose of the present invention, are used interchangeably herein.

An "expression vector" or "expression construct" is any vector that is used to introduce a specific polynucleotide into a target cell such that once the expression vector is inside the cell, the protein that is encoded by the polynucleotide is produced by the cellular transcription and translation machinery. The expressed protein is referred to herein as "operably encoded" by the expression vector. Typically, an expression vector includes regulatory sequences operably linked to the polynucleotide encoding the desired enzyme. Regulatory sequences are common to the person of the skill in the art and may include for example, an origin of replication, a promoter sequence, and/or an enhancer sequence. An expression vector may include a ribosome binding site (RBS) and a start site (e.g., the codon ATG) to initiate translation of the transcribed message to produce the polypeptide. A vector may also include a termination sequence to end translation.

The polynucleotide encoding the desired enzyme can exist extrachromosomally or can be integrated into the host cell chromosomal DNA. Typically, extrachromosomal DNA is maintained within the vector on which it was introduced into the host cell. In many instances, it may be beneficial to select a high copy number vector in order to maximize the expression of the enzyme. The host cell can be a prokaryotic or eukaryotic host cell. An exemplary host cell is Expi293F as described in Example II. Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

The method of the invention further includes expressing the gene product from an uncharacterized NAGLU gene variant in a host cell, and evaluating NAGLU expression levels in order to determine whether the NAGLU gene variant is potentially pathogenic, as exemplified in the Examples.

Kits

Also provided is a kit for detecting an NAGLU activity-reducing mutation or a novel clinically identified mutation in the nucleotide sequence of a human NAGLU gene. In one embodiment, the kit includes at least one oligonucleotide primer specific for an NAGLU activity-reducing NAGLU gene mutation or clinically identified mutation as described herein. In another embodiment, the kit includes at least one allele-specific oligonucleotide probe for an NAGLU activity-reducing NAGLU gene mutation or a clinically identified mutation as described herein. Optionally, the kit includes instructions relating to detecting mutations in the NAGLU gene.

Advantageously, the kit can contain primers or probes of sufficient number and variety so as to screen for a multiplicity of mutations in the nucleotide sequence of the human NAGLU gene, thereby increasing the diagnostic power of the kit. The kit may contain probes and/or primers that are capable of detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more mutations in the nucleotide sequence of a human NAGLU gene.

EXAMPLES

The invention is illustrated by the following example. It is to be understood that the particular examples, materials, amounts, and procedures are to be interpreted broadly in accordance with the scope and spirit of the invention as set forth herein.

Example I. Novel NAGLU Variants Associated with MPS TIM

In four studies (two natural history, one observational, one Phase 1/2), we have obtained NAGLU variant data in most patients as well as dried blood spot testing of NAGLU enzymatic activity. Seven novel NAGLU variants (c.104T>C, c.351delG, c.1012A>G, c.1128_1138del11, c.1621C>T, c.1865T>C, IVS2+5G>A) have been identified in diagnosed patients with MPS IIIB, which may assist in accurate diagnosis. See Table 1.

Dried blood spot testing can utilize MPS III/Sanfilippo enzyme panel, which includes evaluation of N-acetyl-α-D-glucosaminidase activity in order to test for the presence of MPS III, type B. An enzymatic panel can be obtained, for example, from Greenwood Genetic Center (Greenwood, S.C.).

Example II. In Vitro Analysis of NAGLU Variants for Residual Enzymatic Activity

An in vitro biochemical assay is employed to evaluate the residual enzymatic activities of NAGLU variants (e.g., those listed in Table 2). Table 2 includes novel variants described in Example I and elsewhere herein. All but 52 of the variants were previously identified in patients. The remaining 52 potentially pathogenic variants were identified through mining of large population databases, such as the Exome Aggregation Consortium (ExAC) database, and are annotated as "predicted" in Table 2.

TABLE 2

NAGLU Variants

| Plasmid ID | Nucleotide | Protein | |
|---|---|---|---|
| pNAG012 | c.1900G > A | E634K | |
| pNAG013 | c.281_283delinsCCC | R94_D95delinsPH | |
| pNAG014 | c.1834A > G | S612G | |
| pNAG015 | c.1927C > T | R643C | |
| pNAG016 | c.529C > T | R177W | |
| pNAG017 | c.1489C > G | L497V | |
| pNAG018 | c.743A > G | H248R | |
| pNAG019 | c.187G > A | D63N | |
| pNAG020 | c.214-237del24 | A72_G79del8 | |
| pNAG021 | c.1744G > C | A582P | |
| pNAG022 | c.212_214delGCG | G71del | |
| pNAG023 | c.104T > C | L35P | |
| pNAG024 | c.1865T > C | L622P | |
| pNAG025 | c.1012A > G | M338V | |
| pNAG026 | c.1621C > T | R541W | |
| pNAG027 | c.1694G > T | R565L | |
| pNAG028 | c.1212G > C | W404C | |
| pNAG029 | c.507_516del10 | 5169Rfs*13 | |
| pNAG030 | c.2186_2188delAGA | K729delK | |
| pNAG031 | c.813dupT | N272*fs*1 | |
| pNAG032 | c.1128_1138del11 | | |
| pNAG033 | c.351delG | | |
| pNAG034 | c.192delC | Y65Tfs*57 | |
| pNAG035 | c.424_426delTTC | F142del | |
| pNAG036 | c.548G > C | G183A | predicted |
| pNAG037 | c.593T > A | F198Y | predicted |
| pNAG038 | c.642_643delGCinsGCC | S217LfsX56 | predicted |
| pNAG039 | c.642_643delGCinsG | S217PfsX22 | predicted |
| pNAG040 | c.727C > T | P243S | predicted |
| pNAG041 | c.730G > A | A244T | predicted |
| pNAG042 | c.788C > T | T263M | predicted |
| pNAG043 | c.827C > T | S276F | predicted |
| pNAG044 | c.831_835delCTCCTinsC | L280WfsX19 | predicted |
| pNAG045 | c.842T > C | L281P | predicted |
| pNAG046 | c.848delCinsCG | E284GfsX33 | predicted |
| pNAG047 | c.885delC | L296CfsX4 | predicted |
| pNAG048 | c.917A > G | D306G | predicted |
| pNAG049 | c.979C > T | L327F | predicted |
| pNAG050 | c.1052G > C | G351A | predicted |
| pNAG051 | c.1061T > C | F354S | predicted |
| pNAG052 | c.1082G > C | W361S | predicted |
| pNAG053 | c.1120C > T | P374S | predicted |
| pNAG054 | c.1136_1137insG | V380GfsX7 | predicted |
| pNAG055 | c.1154C > T | A385V | predicted |
| pNAG056 | c.1156G > A | E386K | predicted |
| pNAG057 | c.1196G > T | G399V | predicted |
| pNAG058 | c.1222C > T | H408Y | predicted |
| pNAG059 | c.1277G > C | G426A | predicted |
| pNAG060 | c.1291C > T | R431C | predicted |
| pNAG061 | c.1304A > C | N435T | predicted |
| pNAG062 | c.1360G > T | V454F | predicted |
| pNAG063 | c.1364A > C | Y455S | predicted |
| pNAG064 | c.1384G > C | G462R | predicted |
| pNAG065 | c.1390C > T | R464X | predicted |
| pNAG066 | c.1441C > T | R481W | predicted |
| pNAG067 | c.1446delGinsGT | Y483LfsX33 | predicted |
| pNAG068 | c.1449_1450insG | V485GfsX31 | predicted |
| pNAG069 | c.1478C > T | A493V | predicted |
| pNAG070 | c.1487T > C | L496P | predicted |
| pNAG071 | c.1495C > T | R499W | predicted |
| pNAG072 | c.1508A > G | N503S | predicted |
| pNAG073 | c.1538A > G | N513S | predicted |
| pNAG074 | c.1565C > T | S522F | predicted |
| pNAG075 | c.1606G > A | V536M | predicted |
| pNAG076 | c.1675G > A | D559N | predicted |
| pNAG077 | c.1688T > A | L563H | predicted |
| pNAG078 | c.1783G > A | G595R | predicted |
| pNAG079 | c.1786G > T | G596C | predicted |
| pNAG080 | c.1918C > T | Q640X | predicted |
| pNAG081 | c.1934A > C | Q645P | predicted |
| pNAG082 | c.1946G > C | W649S | predicted |
| pNAG083 | c.2017C > T | P673S | predicted |
| pNAG085 | c.2191T > G | F731V | predicted |
| pNAG086 | c.2207C > T | P736L | predicted |
| pNAG087 | c.2229G > A | W743X | predicted |
| pNAG088 | c.100G > C | A34P | |

TABLE 2-continued

NAGLU Variants

| Plasmid ID | Nucleotide | Protein |
|---|---|---|
| pNAG089 | c.1013T > C | M338T |
| pNAG090 | c.1354G > A | E452K |
| pNAG091 | c.1445G > A | R482Q |
| pNAG092 | c.1444C > T | R482W |
| pNAG093 | c.14C > T | A5V |
| pNAG094 | c.1558C > T | R520W |
| pNAG095 | c.1547C > G | P516R |
| pNAG096 | c.1674C > G | Y558X |
| pNAG097 | c.1597C > T | R533X |
| pNAG098 | c.1625T > C | L542P |
| pNAG099 | c.1675G > C | D559H |
| pNAG100 | c.1946G > A | W649X |
| pNAG101 | c.2158C > T | R720X |
| pNAG102 | c.2164G > A | D722N |
| pNAG103 | c.217G > C | A73P |
| pNAG104 | c.2209C > A | R737S |
| pNAG105 | c.2209C > G | R737G |
| pNAG106 | c.299A > G | H100R |
| pNAG107 | c.259G > C | A87P |
| pNAG108 | c.358G > T | E120X |
| pNAG110 | c.625A > C | T209P |
| pNAG111 | c.700C > G | R234G |
| pNAG112 | c.814_820dup | S274X |
| pNAG113 | c.934G > A | D312N |
| pNAG114 | c.1039_1040delTG | W347Afs*39 |
| pNAG115 | c.1691_1694dupCTCG | Q566Sfs*13 |
| pNAG116 | c.171_174dupTGCC | K59Cfs*134 |
| pNAG117 | c.1815_1821dupACTGGAC | E608Tfs*7 |
| pNAG118 | c.1928_1932dupGCTAC | Q645Afs*4 |
| pNAG119 | c.193delT | Y65Tfs*57 |
| pNAG120 | c.1951_1954dupCCAG | E652Afs*34 |
| pNAG121 | c.1004A > G | Y335C |
| pNAG122 | c.1006G > T | E336X |
| pNAG123 | c.103C > T | L35F |
| pNAG124 | c.1000G > T | V334F |
| pNAG125 | c.112C > T | R38W |
| pNAG126 | c.1229T > C | F410S |
| pNAG127 | c.1235G > A | G412E |
| pNAG128 | c.1241A > G | H414R |
| pNAG129 | c.1310C > T | T437I |
| pNAG130 | c.1322C > A | T441K |
| pNAG131 | c.1336G > A | E446K |
| pNAG132 | c.1420T > G | W474G |
| pNAG133 | c.144C > A | F48L |
| pNAG134 | c.1482G > A | W494X |
| pNAG135 | c.1547C > T | P516L |
| pNAG136 | c.1502T > G | V501G |
| pNAG137 | c.1601C > A | S534Y |
| pNAG138 | c.1682T > G | L561R |
| pNAG139 | c.1693C > T | R565W |
| pNAG140 | c.1694G > A | R565Q |
| pNAG141 | c.1811C > T | P604L |
| pNAG142 | c.1831G > C | A611P |
| pNAG143 | c.1851G > C | L617F |
| pNAG144 | c.1915G > T | E639X |
| pNAG145 | c.1946G > T | W649L |
| pNAG146 | c.1947G > C | W649C |
| pNAG147 | c.1949G > A | G650E |
| pNAG148 | c.1973A > T | Y658F |
| pNAG149 | c.2021G > A | R674H |
| pNAG150 | c.205G > A | G69S |
| pNAG151 | c.208G > C | G70R |
| pNAG152 | c.220dupC | R74Pfs*118 |
| pNAG153 | c.38_39insC | L14Sfs*178 |
| pNAG154 | c.410_413delCGCA | T137Kfs*17 |
| pNAG155 | c.507_515delCGGCCAGGA | S169_E172delinsR |
| pNAG156 | c.54_60dupCGGGGGC | A21Rfs*173 |
| pNAG157 | c.651dupC | W218Lfs*55 |
| pNAG158 | c.902_903delAA | K301Rfs*15 |
| pNAG159 | c.905_906delAG | E302Vfs*14 |
| pNAG160 | c.950_951insAA | M317Ifs*23 |
| pNAG161 | c.230T > G | V77G |
| pNAG162 | c.245G > A | G82D |
| pNAG163 | c.388C > T | R130C |
| pNAG164 | c.422C > T | S141F |
| pNAG165 | c.441G > A | W147X |
| pNAG166 | c.461T > G | I154R |
| pNAG167 | c.468G > T | W156C |
| pNAG168 | c.482G > A | G161D |
| pNAG169 | c.680G > C | H227P |
| pNAG170 | c.721G > A | V241M |
| pNAG171 | c.725T > C | L242P |
| pNAG172 | c.728C > T | P243L |
| pNAG173 | c.830G > T | C277F |
| pNAG174 | c.839G > C | L280P |
| pNAG175 | c.926A > G | Y309C |
| pNAG176 | c.940T > C | F314L |
| pNAG177 | c.142T > C | F48L |
| pNAG178 | c.235G > A | G79S |
| pNAG179 | c.1679T > C | L560P |
| pNAG180 | c.736G > C | A246P |
| pNAG181 | c.1694G > C | R565P |
| pNAG182 | c.630G > C | W210C |
| pNAG183 | c.334delC | R112Gfs*10 |
| pNAG184 | c.504delG | W168*fs*1 |
| pNAG185 | c.233_234insGCGGCGCGGCGCGCGTGCGGGTGC | R78_G79insRRGARAGA |
| pNAG186 | c.814_816delAACinsTAA | N272X |
| pNAG187 | c.222_247del26 | V75Gfs*108 |
| pNAG188 | c.903delA | E302Sfs*37 |
| pNAG189 | c.241A > G | T81A |
| pNAG190 | c.392A > C | Y131S |
| pNAG191 | c.410C > T | T137M |
| pNAG192 | c.432G > A | W144X |
| pNAG193 | c.461T > C | I154T |
| pNAG194 | c.472G > T | A158S |
| pNAG195 | c.845C > T | A282V |
| pNAG196 | c.1991C > T | A664V |
| pNAG197 | c.214-237dup24 | A72_G79dup8 |
| pNAG198 | c.457G > A | E153K |
| pNAG199 | c.2113G > A | E705K |
| pNAG200 | c.942C > G | F314L |
| pNAG201 | c.143T > G | F48C |
| pNAG202 | c.874G > A | G292R |
| pNAG203 | c.911G > T | G304V |
| pNAG204 | c.235G > T | G79C |
| pNAG205 | c.1208T > C | I403T |
| pNAG206 | c.1772T > C | L591P |
| pNAG207 | c.200T > C | L67P |
| pNAG208 | c.2045T > G | L682R |
| pNAG209 | c.343C > T | P115S |
| pNAG210 | c.1073C > T | P358L |
| pNAG211 | c.1562C > T | P521L |
| pNAG212 | c.2116C > T | Q706X |
| pNAG213 | c.607C > T | R203X |
| pNAG214 | c.700C > T | R234C |
| pNAG215 | c.889C > T | R297X |
| pNAG216 | c.1876C > T | R626X |
| pNAG217 | c.1928G > A | R643H |
| pNAG218 | c.2020C > T | R674C |
| pNAG219 | c.2027G > C | R676P |
| pNAG220 | c.1564T > C | S522P |
| pNAG221 | c.217_221dupGCGCG | V75Rfs*49 |
| pNAG222 | c.802T > C | W268R |
| pNAG223 | c.1081T > C | W361R |
| pNAG224 | c.1211G > A | W404X |
| pNAG225 | c.2024G > A | W675X |
| pNAG226 | c.419A > G | Y140C |
| pNAG227 | c.1172A > G | Y391C |
| pNAG228 | c.1364A > G | Y455C |
| pNAG229 | c.274T > C | Y92H |
| pNAG230 | c.1487delT | L496Hfs*30 |
| pNAG231 | c.204delC | G69Afs*53 |
| pNAG232 | c.407_410del4 | S169Rfs*16 |
| pNAG233 | c.507delC | S169Rfs*16 |
| pNAG234 | c.703delT | S235Pfs*4 |
| pNAG235 | c.1317delA | G440Afs*36 |
| pNAG236 | c.1335delC | E446Rfs*30 |
| pNAG237 | c.1447dupT | Y483Lfs*33 |
| pNAG238 | c.1932-1933insGCTAC | |

TABLE 2-continued

NAGLU Variants

| Plasmid ID | Nucleotide | Protein |
|---|---|---|
| pNAG241 | c.219_234del19 | R74Pfs*42 |
| pNAG242 | c.334_358del25 | R112Sfs*2 |
| pNAG243 | c.59delG | G20Afs*102 |
| pNAG244 | c.867delC | I290Sfs*10 |
| pNAG246 | c.503G > A | W168X |
| pNAG247 | c.660delC | K221Sfs*18 |

Expression of NAGLU Variants

Plasmids encoding wild-type (WT) NAGLU and NAGLU variants with C-terminal 6× histidine tags were ordered from Thermo Fisher Scientific GeneArt (Regensburg, Germany). Plasmids were sequence verified to confirm the presence of desired mutations. Constructs were transiently transfected into Expi293F cells using ExpiFectamine 293 and the methodology recommended by the manufacturer (Thermo Fisher Scientific, Carlsbad, Calif.). Transfections were carried out at the two milliliter scale in 12-well tissue culture plates (Fisher Scientific, Waltham, Mass.). Transfected cultures were harvested three days post-transfection. Briefly, cultures were spun down at 500×g for five minutes, supernatants transferred to fresh plates, and cell pellets washed twice in phosphate-buffered saline (PBS, GE Healthcare, Marlborough, Mass.). Transfected cultures were incubated with 0.5 mL lysis buffer [1% Triton X-100, 10 mM Sodium Phosphate (pH 7.0), 10 mM dithiothreitol (DTT) and 1 mM ethylenediaminetetraacetic acid (EDTA) in water] for 45 minutes at 4° C. and centrifuged for 15 minutes at 3,000×g to remove insoluble materials.

Western Blot

Cell lysates and supernatants from transfected cultures were mixed with 4×E-PAGE loading buffer and run on 48-well E-PAGE 8% Protein Gels (Thermo Fisher Scientific). Proteins were transferred to polyvinylidene fluoride (PVDF) membranes (Thermo Fisher Scientific), which were incubated overnight in blocking buffer [1% bovine serum albumin (BSA), 0.05% Tween-20 (both Sigma-Aldrich, St. Louis, Mo.) in PBS] at 4° C. Membranes were probed with 1 µg/mL of mouse monoclonal anti-6× his tag antibody (Abcam, Cambridge, Mass.) in wash buffer [0.3% BSA, 0.05% Tween-20 in PBS] for 60 minutes, washed five times, incubated with 0.1 µg/mL IRDye 680RD Donkey anti-mouse IgG (H+L) (LiCor, Lincoln, Nebr.) for thirty minutes and washed four times in wash buffer and once in PBS. His-tagged proteins were detected by near-infrared fluorescence of the secondary antibody using the Odyssey CLx (LiCor).

NAGLU Enzyme Assay

Cell lysate or supernatant from transfected cells (40 µl) was transferred to a black 384 well Optiplate (Perkin Elmer, Waltham, Mass.). The NAGLU enzyme reaction was started by adding 20 µl of the substrate 4-methylumbelliferyl-N-acetyl-α-D-glucosaminide (EMD Millipore/SigmaAldrich) in 1× assay buffer [100 mM Sodium Acetate (pH 5.5) and 250 mM NACl] at a final concentration of 375 µM. 4-methylumbelliferyl N-acetyl-α-D-glucosaminide is also known as 4-methylumbelliferyl 2-acetamido-2-deoxy-α-D-glucopyranoside, (MUG), and is available from Santa Cruz Biotechnology as well. The final reaction volume was 60 µl. A BioTek Synergy 2 plate reader was used to follow 4-methylumbelliferyl fluorophore production at excitation/emission wavelengths of 360/460+/−40 nm. The initial velocity for each NAGLU variant was determined from the first 1 to 2 hours of the reaction. Total protein for each variant was determined (Pierce BCA protein assay kit) and activity was normalized to WT protein levels. Variant NAGLU activity was then compared to WT NAGLU activity.

Example III. Variant Analysis and In Silico Prediction of Mutation Severity

Methods

Allelic variants of NAGLU in patients enrolled in 3 clinical studies (2 natural history and 1 phase I/II) of the SBC-103 (rhNAGLU enzyme) clinical program were analyzed. NGLU-NH01 is a natural history study of deceased MPS TIM patients. Historical mutational data from local laboratories was available from 8 of the 30 patients included in the retrospective study. NGLU-NH02 is a prospective natural history study of MPS IIIB patients (30 patients). NGLU-CL02 is an ongoing phase I/II investigational study of SBC-103 in MPS IIIB patients (11 patients).

In NGLU-NH02 and NGLU-CL02 studies, a blood sample for DNA extraction was collected from each subject and isolation of DNA and genetic mutation analysis for allelic variants of the NAGLU gene was performed.

Four in silico prediction methods (MutationTaster, PolyPhen2, SIFT, and Provean) were utilized to assess the severity of missense mutations and to predict the impact of the mutation on NAGLU enzymatic activity. Missense mutations were flagged based on a consensus score of the four methods. A mutation was flagged as "deleterious" if all four methods predicted it as "deleterious," otherwise it was flagged as "benign."

Results

A total of 53 unique NAGLU variants were identified in 49 patients whose genetic data were available. Of the 53 mutations, 45 variants were identified previously and 8 are novel variants (Table 3). Example II shows 7 of the 8 novel variants; this study identified an additional novel variant, namely, c.1700_1708del9, resulting in an in frame deletion, A567_Q569del.

TABLE 3

Novel NAGLU Variants Identified in Patients

| Nucleotide | Variant type | Amino acid | Domain(s) affected | In silico prediction |
|---|---|---|---|---|
| c.1012A > G | missense | M338V | TIM barrel | deleterious |
| c.1621C > T | missense | R541W | C-terminal | benign |
| c.1865T > C | missense | L622P | C-terminal | deleterious |
| IVS2 + 5G > A[a] | splice variant | | TIM barrel, C-terminal | |
| c.104T > C | missense | L35P | before N-terminal | deleterious |
| c.1128_1138del11[a] | frameshift | | TIM barrel, C-terminal | |
| c.351delG[a] | frameshift | | TIM barrel, C-terminal | |
| c.1700_1708del9 | in frame deletion | A567_Q569del | C-terminal | |

[a]For frameshift and spice variants, the affected domain(s) theoretically starts where the variant is, and extends to the end of the protein.

No highly enriched variant was observed: the majority of the variants (39), including all novel variants, were present only once in this patient group, whereas the other 14 variants were present multiple times with c.419A>G as the most frequent allele at 5 times (Table 4).

TABLE 4

NAGLU Variants That Were Identified More Than One Time in Patients

| Nucleotide | Variant type | Amino acid | Domain(s) affected | Frequency |
|---|---|---|---|---|
| c.419A > G | missense | Y140C | TIM barrel | 5 |
| c.700C > T | missense | R234C | TIM barrel | 4 |
| c.1211G > A | nonsense | W404X | TIM barrel | 4 |
| c.874G > A | missense | G292R | TIM barrel | 4 |
| c.889C > T | nonsense | R297X | TIM barrel, C-terminal | 3 |
| c.1694G > A | missense | R565Q | C-terminal | 2 |
| c.1562C > T | missense | P521L | C-terminal | 2 |
| c.503G > A | nonsense | W168X | TIM barrel, C-terminal | 2 |
| c.507_516del10 | frameshift | | TIM barrel, C-terminal | 2 |
| c.1834A > G | missense | S612G | C-terminal | 2 |
| c.2186_2188delAGA | in-frame deletion | K729del | C-terminal end | 2 |
| c.889C > T | nonsense | R297X | TIM barrel, C-terminal | 2 |
| c.212_214delGCG | in-frame deletion | G71del | N-terminal | 2 |
| c.192delC | frameshift | | N-terminal, TIM barrel, C-terminal | 2 |

NAGLU has three conserved domains: an N-terminal domain spanning amino acids 42-116; a TIM barrel domain spanning amino acids 130-465; and a C-terminal domain spanning amino acids 474-729. As shown in FIG. 3, all but one (c.104T>C) of the 53 NAGLU variant mutations are located in one of the three conserved domains in the NAGLU enzyme. Mutations may affect one or more domains of the protein. About half of the mutations are present in the TIM barrel domain and another half in the C-terminal domain; 6 mutations affect only the N-terminal domain.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference.

The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

---

What is claimed is:

1. A method of detecting a mutation in a nucleotide sequence of a human N-acetyl-alpha-D-glucosaminidase (NAGLU) gene, the method comprising:
   (a) obtaining a biological sample comprising a human nucleic acid; and
   (b) detecting within the biological sample a mutation in a human NAGLU nucleotide sequence, wherein the mutation comprises a nucleotide sequence mutation encoding a L35P amino acid substitution at amino acid position L35 relative to a wild-type NAGLU amino acid sequence consisting of SEQ ID NO:1.

2. The method of claim 1, wherein detecting within the biological sample a mutation in a human NAGLU nucleotide sequence comprises performing whole transcriptome sequencing, whole exome sequencing, whole genome sequencing, or hybridization to a DNA microarray.

3. The method of claim 1, wherein the mutation encoding the L35P amino acid substitution at amino acid position L35 comprises a nucleotide sequence mutation c.104T>C relative to a wild-type human NAGLU cDNA sequence consisting of SEQ ID NO:2.

4. The method of claim 1, further comprising detecting within the biological sample the presence of a second mutation in a human NAGLU nucleotide sequence.

5. A method for treating Mucopolysaccharidosis IIIB (MPS IIIB) in a patient, the method comprising the steps of:
   (a) obtaining a biological sample comprising a nucleic acid from the patient;
   (b) detecting in the biological sample a mutation in a human N-acetyl-alpha-D-glucosaminidase (NAGLU) nucleotide sequence;
   wherein the mutation comprises a nucleotide sequence mutation encoding an L35P amino acid substitution at amino acid position L35 relative to a wild-type human NAGLU amino acid sequence consisting of (SEQ ID NO:1);
   (c) diagnosing the patient with MPS IIIB when the nucleotide sequence mutation encoding the L35P amino acid substitution at amino acid position L35 relative to the wild-type human NAGLU amino acid sequence consisting of SEQ ID NO:1 is detected in the biological sample; and
   (d) administering a therapeutically effective amount of exogenous NAGLU to the diagnosed patient.

6. The method of claim 5, wherein the nucleotide sequence mutation encoding the L35P amino acid substitution at amino acid position L35 comprises a nucleotide sequence mutation c.104T>C relative to a wild-type human NAGLU cDNA sequence consisting of SEQ ID NO:2.

7. The method of claim 5, wherein detecting a mutation in the human NAGLU nucleotide sequence comprises performing whole transcriptome sequencing, whole exome sequencing, whole genome sequencing, or hybridization to a DNA microarray.

8. The method of claim 5, wherein the patient is a pediatric patient.

9. The method of claim 5, wherein the patient is an adult patient.

10. The method of claim 5, further comprising detecting the presence of a second mutation in a human NAGLU nucleotide sequence in the biological sample.

11. The method of claim 5, wherein the exogenous NAGLU comprises recombinant human NAGLU (rhNAGLU).

12. The method of claim 5, wherein the exogenous NAGLU comprises N-linked glycan structures comprising at least one mannose and/or mannose-6-phosphate.

13. A method treating Mucopolysaccharidosis IIIB (MPS IIIB) in a human patient, the method comprising:
    detecting a nucleotide sequence mutation encoding an L35P amino acid substitution at amino acid position L35 relative to a wild-type human N-acetyl-alpha-D-glucosaminidase (NAGLU) amino acid sequence consisting of SEQ ID NO:1 in a nucleotide sequence of a human NAGLU gene of the patient;
    diagnosing the patient with MPS IIIB when the nucleotide sequence mutation encoding the L35P amino acid substitution at amino acid position L35 relative to the wild-type human NAGLU amino acid sequence consisting of SEQ ID NO:1 is detected in the nucleotide sequence of the human NAGLU gene of the patient; and
    administering a therapeutically effective amount of exogenous NAGLU to the diagnosed patient.

14. The method of claim 13, wherein the nucleotide sequence mutation encoding the L35P amino acid substitution at amino acid position L35 comprises a nucleotide sequence mutation c.104T>C relative to a wild-type human NAGLU cDNA sequence consisting of SEQ ID NO:2.

15. The method of claim 13, wherein detecting whether a mutation in a human NAGLU nucleotide sequence is present in the biological sample comprises performing whole transcriptome sequencing, whole exome sequencing, whole genome sequencing, or hybridization to a DNA microarray.

16. The method of claim 13, wherein the patient is a pediatric patient.

17. The method of claim 13, wherein the patient is an adult patient.

18. The method of claim 13, further comprising detecting the presence of a second mutation in a human NAGLU nucleotide sequence in the biological sample.

19. The method of claim 13, wherein the exogenous NAGLU comprises recombinant human NAGLU (rhNAGLU).

20. The method of claim 13, wherein the exogenous NAGLU comprises N-linked glycan structures comprising at least one mannose and/or mannose-6-phosphate.

* * * * *

SEQUENCE LISTING

```
<160> NUMBER OF SEQ ID NOS: 3

<210> SEQ ID NO 1
<211> LENGTH: 743
<212> TYPE: PRT
<213> ORGANISM: homo sapien

<400> SEQUENCE: 1

Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
                35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
                180                 185                 190
```

```
Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
        210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
                260                 265                 270

Cys Ser Tyr Ser Cys Ser Phe Leu Leu Ala Pro Glu Asp Pro Ile Phe
            275                 280                 285

Pro Ile Ile Gly Ser Leu Phe Leu Arg Glu Leu Ile Lys Glu Phe Gly
            290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Thr Thr Ala Val Tyr Glu
                325                 330                 335

Ala Met Thr Ala Val Asp Thr Glu Ala Val Trp Leu Leu Gln Gly Trp
                340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
            370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
            435                 440                 445

Ser Gln Asn Glu Val Val Tyr Ser Leu Met Ala Glu Leu Gly Trp Arg
            450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
            515                 520                 525

Ile Trp Tyr Asn Arg Ser Asp Val Phe Glu Ala Trp Arg Leu Leu Leu
            530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
                580                 585                 590

Arg Ala Gly Gly Val Leu Ala Tyr Glu Leu Leu Pro Ala Leu Asp Glu
            595                 600                 605
```

Val Leu Ala Ser Asp Ser Arg Phe Leu Leu Gly Ser Trp Leu Glu Gln
610                 615                 620

Ala Arg Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
                660                 665                 670

Pro Arg Trp Arg Leu Phe Leu Glu Ala Leu Val Asp Ser Val Ala Gln
                675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 2
<211> LENGTH: 2232
<212> TYPE: DNA
<213> ORGANISM: homo sapien

<400> SEQUENCE: 2

| | | | | |
|---|---|---|---|---|
| atggaggcgg | tggcggtggc | cgcggcggtg | ggggtccttc | tcctggccgg | ggccggggc | 60 |
| gcggcaggcg | acgaggcccg | ggaggcggcg | gccgtgcggg | cgctcgtggc | ccggctgctg | 120 |
| gggccaggcc | ccgcggccga | cttctccgtg | tcggtggagc | gcgctctggc | tgccaagccg | 180 |
| ggcttggaca | cctacagcct | gggcggcggc | ggcgcggcgc | cgtgcgggt | gcgcggctcc | 240 |
| acgggcgtgg | cggccgccgc | ggggctgcac | cgctacctgc | gcgacttctg | tggctgccac | 300 |
| gtggcctggt | ccggctctca | gctgcgcctg | ccgcggccac | tgccagccgt | gccggggag | 360 |
| ctgaccgagg | ccacgcccaa | caggtaccgc | tattaccaga | atgtgtgcac | gcaaagctac | 420 |
| tctttcgtgt | ggtgggactg | ggcccgctgg | gagcgagaga | tagactggat | ggcgctgaat | 480 |
| ggcatcaacc | tggcactggc | ctggagcggc | caggaggcca | tctggcagcg | ggtgtacctg | 540 |
| gccttgggcc | tgacccaggc | agagatcaat | gagttctta | ctggtcctgc | cttcctggcc | 600 |
| tgggggcgaa | tgggcaacct | gcacacctgg | gatggccccc | tgcccccctc | ctggcacatc | 660 |
| aagcagcttt | acctgcagca | ccgggtcctg | gaccagatgc | gctccttcgg | catgaccca | 720 |
| gtgctgcctg | cattcgcggg | gcatgttccc | gaggctgtca | ccagggtgtt | ccctcaggtc | 780 |
| aatgtcacga | agatgggcag | ttggggccac | tttaactgtt | cctactcctg | ctccttcctt | 840 |
| ctggctccgg | aagaccccat | attccccatc | atcgggagcc | tcttcctgcg | agagctgatc | 900 |
| aaagagtttg | gcacagacca | catctatggg | gccgacactt | tcaatgagat | gcagccacct | 960 |
| tcctcagagc | cctcctacct | tgccgcagcc | accactgccg | tctatgaggc | catgactgca | 1020 |
| gtggatactg | aggctgtgtg | gctgctccaa | ggctggctct | ccagcacca | gccgcagttc | 1080 |
| tgggggcccg | cccagatcag | ggctgtgctg | ggagctgtgc | ccgtggccg | cctcctggtt | 1140 |
| ctggacctgt | tgctgagag | ccagcctgtg | tatacccgca | ctgcctcctt | ccagggccag | 1200 |
| cccttcatct | ggtgcatgct | gcacaacttt | ggggaaacc | atggtctttt | tggagcccta | 1260 |
| gaggctgtga | acggaggccc | agaagctgcc | cgcctcttcc | ccaactccac | catggtaggc | 1320 |

```
acgggcatgg ccccogaggg catcagccag aacgaagtgg tctattccct catggctgag    1380
ctgggctggc gaaaggaccc agtgccagat ttggcagcct gggtgaccag ctttgccgcc    1440
cggcggtatg gggtctccca cccggacgca ggggcagcgt ggaggctact gctccggagt    1500
gtgtacaact gctccggga ggcctgcagg ggccacaatc gtagcccgct ggtcaggcgg     1560
ccgtccctac agatgaatac cagcatctgg tacaaccgat ctgatgtgtt tgaggcctgg    1620
cggctgctgc tcacatctgc tccctccctg gccaccagcc ccgccttccg ctacgacctg    1680
ctggacctca ctcggcaggc agtgcaggag ctggtcagct tgtactatga ggaggcaaga    1740
agcgcctacc tgagcaagga gctggcctcc ctgttgaggg ctggaggcgt cctggcctat    1800
gagctgctgc cggcactgga cgaggtgctg gctagtgaca gccgcttctt gctgggcagc    1860
tggctagagc aggcccgagc agcggcagtc agtgaggccg aggccgattt ctacgagcag    1920
aacagccgct accagctgac cttgtggggg ccagaaggca acatcctgga ctatgccaac    1980
aagcagctgg cggggttggt ggccaactac tacacccctc gctggcggct tttcctggag    2040
gcgctggttg acagtgtggc ccagggcatc cctttccaac agcaccagtt tgacaaaaat    2100
gtcttccaac tggagcaggc cttcgttctc agcaagcaga ggtaccccag ccagccgcga    2160
ggagacactg tggacctggc caagaagatc ttcctcaaat attaccccg ctgggtggcc     2220 ggctcttggt ga                                                        2232

<210> SEQ ID NO 3
<211> LENGTH: 23
<212> TYPE: PRT
<213> ORGANISM: homo sapien

<400> SEQUENCE: 3

Met Glu Ala Val Ala Val Ala Ala Ala Val Gly Val Leu Leu Leu Ala
1               5                   10                  15

Gly Ala Gly Gly Ala Ala Gly
            20
```